(12) United States Patent
Hayter et al.

(10) Patent No.: US 11,749,410 B2
(45) Date of Patent: Sep. 5, 2023

(54) DYNAMIC DISPLAY OF GLUCOSE INFORMATION

(71) Applicant: Abbott Diabetes Care Inc., Alameda, CA (US)

(72) Inventors: Gary Alan Hayter, Oakland, CA (US); Timothy Christian Dunn, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 878 days.

(21) Appl. No.: 15/468,156

(22) Filed: Mar. 24, 2017

(65) Prior Publication Data

US 2017/0193184 A1 Jul. 6, 2017

Related U.S. Application Data

(63) Continuation of application No. 14/981,863, filed on Dec. 28, 2015, which is a continuation of application
(Continued)

(51) Int. Cl.
*G16H 50/50* (2018.01)
*G06K 9/00* (2022.01)
(Continued)

(52) U.S. Cl.
CPC ............ *G16H 50/50* (2018.01); *A61M 5/142* (2013.01); *A61M 5/1723* (2013.01);
(Continued)

(58) Field of Classification Search
CPC ......... G16H 50/50; G16H 40/63; H04W 4/80; A61M 5/1723; A61M 5/142;
(Continued)

(56) References Cited

U.S. PATENT DOCUMENTS 5,569,186 A 10/1996 Lord et al.
5,665,065 A 9/1997 Colman et al.
(Continued)

FOREIGN PATENT DOCUMENTS

WO    WO 99/56613 A1    11/1999
WO    WO 2004/009161 A1    1/2004
(Continued)

OTHER PUBLICATIONS

PMA Approvals FDA—webpage available at: https://www.fda.gov; 3 pages, Year: 2022.
(Continued)

*Primary Examiner* — Jacqueline Cheng
*Assistant Examiner* — Tho Q Tran
(74) *Attorney, Agent, or Firm* — Sterne, Kessler, Goldstein & Fox P.L.L.C.

(57) ABSTRACT

Method and system including displaying a first representation of a medication treatment parameter profile, displaying a first representation of a physiological profile associated with the medication treatment parameter profile, detecting a modification to a segment of the medication treatment parameter profile, displaying a modified representation of the medication treatment parameter profile and the physiological profile based on the detected modification to the segment of the medication treatment parameter profile, modifying an attribute of the first representation of the medication treatment parameter profile, and modifying an attribute of the first representation of the physiological profile are provided.

11 Claims, 27 Drawing Sheets

Related U.S. Application Data

No. 12/242,799, filed on Sep. 30, 2008, now abandoned, which is a continuation-in-part of application No. 12/024,082, filed on Jan. 31, 2008, now abandoned.

(60) Provisional application No. 61/015,185, filed on Dec. 19, 2007.

(51) Int. Cl.

| | |
|---|---|
| *G16H 20/17* | (2018.01) |
| *A61M 5/142* | (2006.01) |
| *A61M 5/172* | (2006.01) |
| *G16H 40/63* | (2018.01) |
| *H04W 4/80* | (2018.01) |
| *G06F 3/04847* | (2022.01) |
| *G16H 20/60* | (2018.01) |

(52) U.S. Cl.
CPC ......... *G06F 3/04847* (2013.01); *G16H 20/17* (2018.01); *G16H 20/60* (2018.01); *G16H 40/63* (2018.01); *H04W 4/80* (2018.02); *A61M 2005/14208* (2013.01); *A61M 2205/18* (2013.01); *A61M 2205/3584* (2013.01); *A61M 2205/50* (2013.01); *A61M 2205/502* (2013.01); *A61M 2205/52* (2013.01); *A61M 2205/582* (2013.01); *A61M 2230/005* (2013.01); *A61M 2230/201* (2013.01); *G06F 2218/16* (2023.01)

(58) Field of Classification Search
CPC ........ A61M 2205/582; A61M 2205/50; A61M 2205/18; A61M 2230/201; A61M 2230/005; A61M 2205/52; A61M 2205/502; A61M 2205/3584; A61M 2005/14208; G06F 19/3468; G06F 3/04847; G06Q 50/22; G06K 9/0055
See application file for complete search history.

(56) References Cited

U.S. PATENT DOCUMENTS

| | | | |
|---|---|---|---|
| 6,175,752 B1 | 1/2001 | Say et al. | |
| 6,544,212 B2 | 4/2003 | Galley et al. | |
| 2003/0114836 A1 | 6/2003 | Estes et al. | |
| 2005/0038332 A1 | 2/2005 | Saidara et al. | |
| 2005/0187749 A1* | 8/2005 | Singley | G06F 19/3475 703/11 |
| 2006/0276771 A1 | 12/2006 | Galley et al. | |
| 2007/0040449 A1* | 2/2007 | Spurlin | G06F 1/30 307/64 |
| 2007/0060869 A1* | 3/2007 | Tolle | A61M 5/14244 604/65 |
| 2007/0106135 A1 | 5/2007 | Sloan et al. | |
| 2007/0149874 A1 | 6/2007 | Say et al. | |
| 2007/0179370 A1 | 8/2007 | Say et al. | |
| 2007/0208244 A1 | 9/2007 | Brauker et al. | |
| 2008/0119710 A1 | 5/2008 | Reggiardo et al. | |
| 2008/0171967 A1* | 7/2008 | Blomquist | G06F 19/324 604/67 |
| 2008/0235053 A1 | 9/2008 | Ray et al. | |
| 2008/0262469 A1 | 10/2008 | Brister et al. | |
| 2008/0269714 A1* | 10/2008 | Mastrototaro | A61M 5/14244 604/504 |
| 2009/0006133 A1* | 1/2009 | Weinert | G16H 15/00 705/3 |
| 2009/0055149 A1 | 2/2009 | Hayter et al. | |
| 2009/0177147 A1* | 7/2009 | Blomquist | A61M 5/14244 604/67 |
| 2009/0192380 A1 | 7/2009 | Shariati et al. | |
| 2009/0216102 A1 | 8/2009 | Say et al. | |
| 2009/0221890 A1 | 9/2009 | Saffer et al. | |
| 2010/0174266 A1* | 7/2010 | Estes | A61M 5/14244 604/504 |
| 2016/0081632 A1 | 3/2016 | Kamath et al. | |
| 2016/0101232 A1* | 4/2016 | Kamath | A61B 5/14532 604/504 |

FOREIGN PATENT DOCUMENTS

| | | |
|---|---|---|
| WO | WO 2006/079867 A1 | 8/2006 |
| WO | WO 2008/030347 A2 | 3/2008 |

OTHER PUBLICATIONS

PMA database search for Freestyle Navigator Continuous Glucose Monitor—https://www.fda.gov; 6 pages, Year: 2005.

Sparacino, Giovanni et al., "Glucose Concentration can be Predicted Ahead in Time From Continuous Glucose Monitoring Sensor Time-Series," IEEE Transactions on Biomedical Engineering, vol. 54, No. 5, May 2007; 7 pages.

Sandham, William et al., "Blood Glucose Prediction for Diabetes Therapy Using a Recurrent Artificial Neural Network," 9th European Signal Processing Conference (EUSIPCO 1998), 1998, pp. 1-4.

Exhibit CP-6, Second Expert Report of Dr. Cesar C. Palerm, Oct. 21, 2022, Bailey, T.S et al., "Reduction in Hemoglobin A1c with Real-Time Continuous Glucose Monitoring: Results from a 12-Week Observational Study" Diabetes Technology & Therapeutics, 2007, 9(3):203-210.

Exhibit CP-7, Second Expert Report of Dr. Cesar C. Palerm, Oct. 21, 2022, Garg, S et al., "Improvement in Glycemic Excursions with a Transcutaneous, Real-Time Continuous Glucose Sensor", Diabetes Care, Jan. 2006, 29(12):44-50.

Exhibit CP-8, Second Expert Report of Dr. Cesar C. Palerm, Oct. 21, 2022, Garg, S. et al., Relationship of Fasting and Hourly Blood Glucose Levels to HbA1c Values, Diabetes Care, Dec. 2006, 6(12):2644-2649.

Exhibit No. 2, to the Expert Report of Professor Nick Oliver, Sep. 20, 2022, "Note for Guidance on Clinical Investigation of Medicinal Products in the Treatment of Diabetes Mellitus," The European Agency for the Evaluation of Medicinal Products, 2002, 12 pages.

Exhibit No. 3, to the Expert Report of Professor Nick Oliver, Sep. 20, 2022, "Defining and Reporting Hypoglycemia in Diabetes", American Diabetes Association, Diabetes Care, 2005, 28(5):1245-1249.

Exhibit No. 11, to the Expert Report of Professor Nick Oliver, Sep. 20, 2022, "The Effect of Intensive Treatment of Diabetes on the Development and Progression of Long-Term Complications in Insulin-Dependent Diabetes Mellitus" The New England Journal of Medicine, 1993, 329(14):977-986.

Exhibit No. 12, to the Expert Report of Professor Nick Oliver, Sep. 20, 2022, National Service Framework for Diabetes: Standards, Dept. of Health, 2002, 48 pages.

Exhibit No. 13, to the Expert Report of Professor Nick Oliver, Sep. 20, 2022, Amiel, S. et al., "Training in flexible, intensive insulin management to enable dietary freedom in people with type 1 diabetes: dose adjustment for normal eating (DAFNE) randomized controlled trial" BMJ, 2002, 325; 6 pages.

Exhibit No. 14, to the Expert Report of Professor Nick Oliver, Sep. 20, 2022, "Type 1 diabetes: diagnosis and management of type 1 diabetes in children, young people and adults" National Institute for Clinical Excellence, Clinical Guideline 15, Jul. 2004, 113 pages.

Exhibit No. 20, to the Expert Report of Professor Nick Oliver, Sep. 20, 2022, "Continuous Glucose Sensors: Continuing Questions about Clinical Accuracy" Journal of Diabetes Science and Technology, 2007; 1(5):669-675.

Exhibit No. 24, to the Expert Report of Professor Nick Oliver, Sep. 20, 2022, "Glucowatch 62, Automatic Glucose Biographer and Autosensors," 2002, 70 pages.

Exhibit No. 25, to the Expert Report of Professor Nick Oliver, Sep. 20, 2022, "Guardian® Real-Time Continuous Glucose Monitoring System, User Guide," Medtronic MiniMed, 2006, 181 pages.

(56) References Cited

OTHER PUBLICATIONS

Exhibit No. 26, to the Expert Report of Professor Nick Oliver, Sep. 20, 2022, "CGMS® iProTM Continuous Glucose Recorder, User Guide," Medtronic MiniMed, 2007, 36 pages.

Exhibit No. 30, to the Expert Report of Professor Nick Oliver, Sep. 20, 2022, Revised specification for publication No. US2007208244A1, 2007, 170 pages.

Exhibit No. 32, to the Expert Report of Professor Nick Oliver, Sep. 20, 2022, Puhr, S. et al., "Real-World Hypoglycemia Avoidance with a Predictive Low Glucose Alert Does Not Depend on Frequent Screen Views", Journal of Diabetes Sciences and Technology, 2004, 14(1): 83-86.

"Dexcom's 7-Day Continuous Glucose Monitoring System," Jun. 1, 2007, https://newatlas.com/; 1 page.

* cited by examiner

DYNAMIC DISPLAY OF GLUCOSE INFORMATION

RELATED APPLICATIONS

The present application is a continuation of U.S. patent application Ser. No. 14/981,863 filed Dec. 28, 2015, which is a continuation of U.S. patent Ser. No. 12/242,799 filed Sep. 30, 2008, which is a continuation in part of U.S. patent application Ser. No. 12/024,082 filed Jan. 31, 2008 entitled "Method and Apparatus for Providing Treatment Profile Management" which claims priority to U.S. Provisional Application No. 61/015,185 filed Dec. 19, 2007, entitled "Medical Devices and Methods" assigned to the Assignee of the present application, Abbott Diabetes Care Inc., of Alameda, Calif., the disclosure of each of which are incorporated herein by reference for all purposes.

BACKGROUND

Analyte, e.g., glucose, monitoring systems including continuous and discrete monitoring systems generally include a small, lightweight battery powered and microprocessor controlled system which is configured to detect signals proportional to the corresponding measured glucose levels using an electrometer, and radio frequency (RF) signals to transmit the collected data. One aspect of certain analyte monitoring systems include a transcutaneous or subcutaneous analyte sensor configuration which is, for example, partially mounted on the skin of a subject whose analyte level is to be monitored. The sensor cell may use a two or three-electrode (work, reference and counter electrodes) configuration driven by a controlled potential (potentiostat) analog circuit connected through a contact system.

With increasing use of pump therapy for Type 1 diabetic patients, young and old alike, the importance of controlling the infusion device such as external infusion pumps is evident. Indeed, presently available external infusion devices typically include an input mechanism such as buttons through which the patient may program and control the infusion device. Such infusion devices also typically include a user interface such as a display which is configured to display information relevant to the patient's infusion progress, status of the various components of the infusion device, as well as other programmable information such as patient specific basal profiles.

In the course of using the analyte monitoring system and the infusion device, data associated with a patient's physiological condition such as monitored analyte levels, insulin dosage information, for example, may be stored and processed. As the complexity of these systems and devices increase, so do the amount of data and information associated with the system/device.

SUMMARY

In accordance with the various embodiments of the present disclosure, there are provided method system including displaying a first representation of a medication treatment parameter profile, displaying a first representation of a physiological profile associated with the medication treatment parameter profile, detecting a modification to a segment of the medication treatment parameter profile, displaying a modified representation of the medication treatment parameter profile and the physiological profile based on the detected modification to the segment of the medication treatment parameter profile, modifying an attribute of the first representation of the medication treatment parameter profile, and modifying an attribute of the first representation of the physiological profile are provided. These and other objects, features and advantages of the present disclosure will become more fully apparent from the following detailed description of the embodiments, the appended claims and the accompanying drawings.

DETAILED DESCRIPTION

Figure 1:
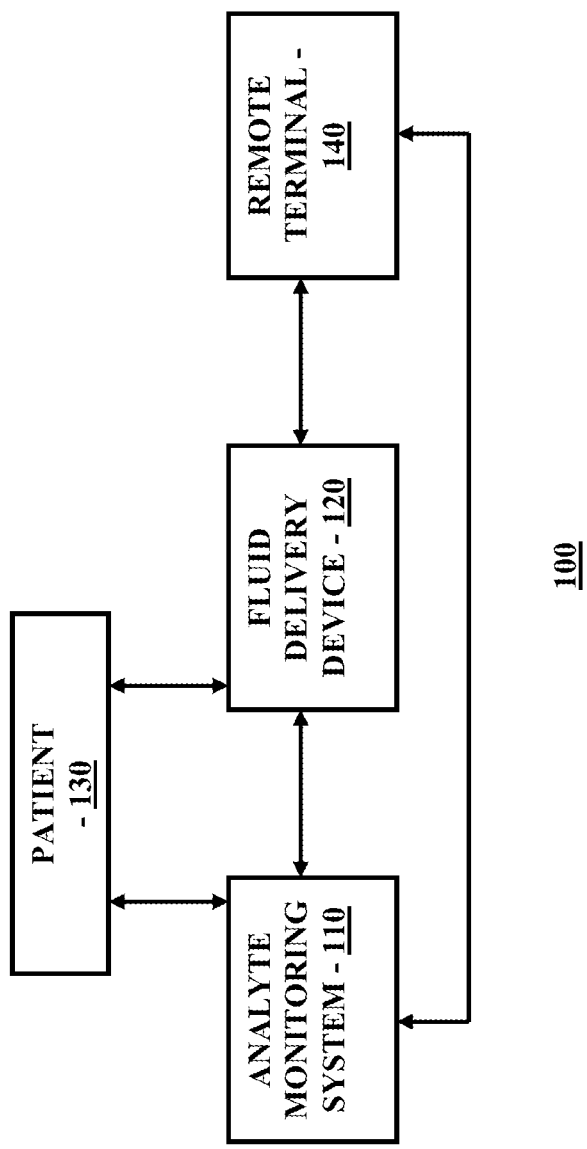
FIG. 1 is a block diagram illustrating a therapy management system for practicing one embodiment of the present disclosure.

FIG. 1 is a block diagram illustrating an insulin therapy management system for practicing one embodiment of the present disclosure. Referring to FIG. 1, the therapy management system 100 includes an analyte monitoring system 110 operatively coupled to a fluid delivery device 120, which may be in turn, operatively coupled to a remote terminal 140. As shown the Figure, the analyte monitoring system 110 is, in one embodiment, coupled to the patient 130 so as to monitor or measure the analyte levels of the patient. Moreover, the fluid delivery device 120 is coupled to the patient using, for example, and infusion set and tubing connected to a cannula (not shown) that is placed transcutaneously through the skin of the patient so as to infuse medication such as, for example, insulin, to the patient.

Referring to FIG. 1, in one embodiment, the analyte monitoring system 110 may include one or more analyte sensors subcutaneously positioned such that at least a portion of the analyte sensors are maintained in fluid contact with the patient's analytes. The analyte sensors may include, but not limited to, short term subcutaneous analyte sensors or transdermal analyte sensors, for example, which are configured to detect analyte levels of a patient over a predetermined time period, and after which, a replacement of the sensors is necessary.

The one or more analyte sensors of the analyte monitoring system 110 is coupled to a respective one or more of a data transmitter unit which is configured to receive one or more signals from the respective analyte sensors corresponding to the detected analyte levels of the patient, and to transmit the information corresponding to the detected analyte levels to a receiver device, and/or fluid delivery device 120. That is, over a communication link, the transmitter units may be configured to transmit data associated with the detected analyte levels periodically, and/or intermittently and repeatedly to one or more other devices such as the insulin delivery device and/or the remote terminal 140 for further data processing and analysis.

The transmitter units of the analyte monitoring system 110 may in one embodiment configured to transmit the analyte related data substantially in real time to the fluid delivery device 120 and/or the remote terminal 140 after receiving it from the corresponding analyte sensors such that the analyte level, such as the glucose level, of the patient 130 may be monitored in real time. In one aspect, the analyte levels of the patient may be obtained using one or more of a discrete blood glucose testing devices such as blood glucose meters, or continuous analyte monitoring systems such as continuous glucose monitoring systems.

Additional analytes that may be monitored, determined or detected by the analyte monitoring system 110 include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Moreover, within the scope of the present disclosure, the transmitter units of the analyte monitoring system 110 may be configured to directly communicate with one or more of the remote terminal 140 or the fluid delivery device 120. Furthermore, within the scope of the present disclosure, additional devices may be provided for communication in the analyte monitoring system 110 including additional receiver/data processing units, and/or remote terminals, such as a physician's terminal and/or a bedside terminal in a hospital environment, for example. In addition, within the scope of the present disclosure, one or more of the analyte monitoring system 110, the fluid delivery device 120 and the remote terminal 140 may be configured to communicate over a wireless data communication link such as, but not limited to, RF communication link, Bluetooth® communication link, infrared communication link, or any other type of suitable wireless communication connection between two or more electronic devices, which may further be unidirectional or bi-directional communication between the two or more devices. Alternatively, the data communication link may include wired cable connection such as, for example, but not limited to, RS232 connection, USB connection, or serial cable connection.

Referring back to FIG. 1, in one embodiment, the analyte monitoring system 110 includes a strip port configured to receive a test strip for capillary blood glucose testing. In one aspect, the glucose level measured using the test strip may in addition, be configured to provide periodic calibration of the analyte sensors of the analyte monitoring system 110 to assure and improve the accuracy of the analyte levels detected by the analyte sensors.

Exemplary analyte systems that may be employed are described in, for example, U.S. Pat. Nos. 6,134,461, 6,175,752, 6,121,611, 6,560,471, 6,746,582, and elsewhere, the disclosures of which are herein incorporated by reference.

Referring again to FIG. 1, the fluid delivery device 120 may include in one embodiment, but not limited to, an external infusion device such as an external insulin infusion pump, an implantable pump, a pen-type insulin injector device, an on-body patch pump, an inhalable infusion device for nasal insulin delivery, or any other type of suitable delivery system. In addition, the remote terminal 140 in one embodiment may include for example, a desktop computer terminal, a data communication enabled kiosk, a laptop computer, a handheld computing device such as a personal digital assistant (PDAs), or a data communication enabled mobile telephone.

Figure 2:
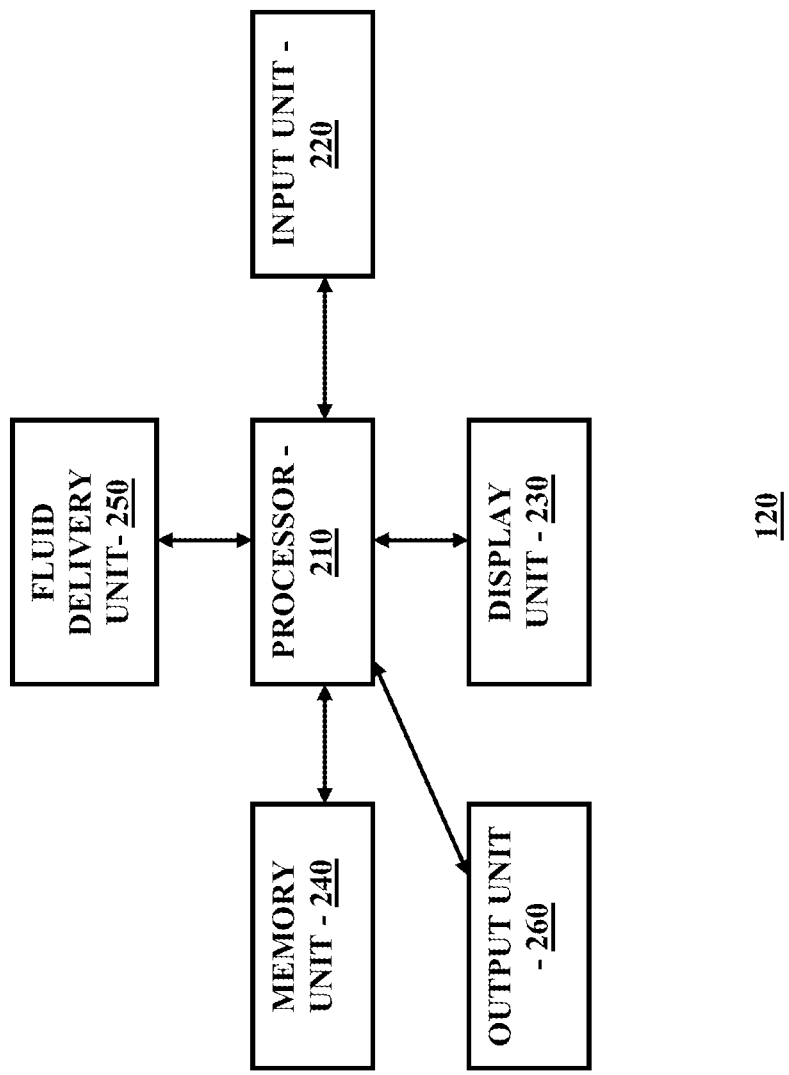
FIG. 2 is a block diagram of a fluid delivery device of FIG. 1 in one embodiment of the present disclosure.

FIG. 2 is a block diagram of an insulin delivery device of FIG. 1 in one embodiment of the present disclosure. Referring to FIG. 2, the fluid delivery device 120 in one embodiment includes a processor 210 operatively coupled to a memory unit 240, an input unit 220, a display unit 230, an output unit 260, and a fluid delivery unit 250. In one embodiment, the processor 210 includes a microprocessor that is configured to and capable of controlling the functions of the fluid delivery device 120 by controlling and/or accessing each of the various components of the fluid delivery device 120. In one embodiment, multiple processors may be provided as safety measure and to provide redundancy in case of a single processor failure. Moreover, processing capabilities may be shared between multiple processor units within the insulin delivery device 120 such that pump functions and/or control maybe performed faster and more accurately.

Referring back to FIG. 2, the input unit 220 operatively coupled to the processor 210 may include a jog dial, key pad buttons, a touch pad screen, or any other suitable input mechanism for providing input commands to the fluid delivery device 120. More specifically, in case of a jog dial input device, or a touch pad screen, for example, the patient or user of the fluid delivery device 120 will manipulate the respective jog dial or touch pad in conjunction with the display unit 230 which performs as both a data input and output units. The display unit 230 may include a touch sensitive screen, an LCD screen, or any other types of suitable display unit for the fluid delivery device 120 that is configured to display alphanumeric data as well as pictorial information such as icons associated with one or more predefined states of the fluid delivery device 120, or graphical representation of data such as trend charts and graphs associated with the insulin infusion rates, trend data of monitored glucose levels over a period of time, or textual notification to the patients.

Referring to FIG. 2, the output unit 260 operatively coupled to the processor 210 may include audible alarm including one or more tones and/or preprogrammed or programmable tunes or audio clips, or vibratory alert features having one or more pre-programmed or programmable vibratory alert levels. In one embodiment, the vibratory alert may also assist in priming the infusion tubing to minimize the potential for air or other undesirable material in the infusion tubing. Also shown in FIG. 2 is the fluid delivery unit 250 which is operatively coupled to the processor 210 and configured to deliver the insulin doses or amounts to the patient from the insulin reservoir or any other types of suitable containment for insulin to be delivered (not shown) in the fluid delivery device 120 via an infusion set coupled to a subcutaneously positioned cannula under the skin of the patient.

Referring yet again to FIG. 2, the memory unit 240 may include one or more of a random access memory (RAM), read only memory (ROM), or any other types of data storage units that is configured to store data as well as program instructions for access by the processor 210 and execution to control the fluid delivery device 120 and/or to perform data processing based on data received from the analyte monitoring system 110, the remote terminal 140, the patient 130 or any other data input source.

Figure 3:
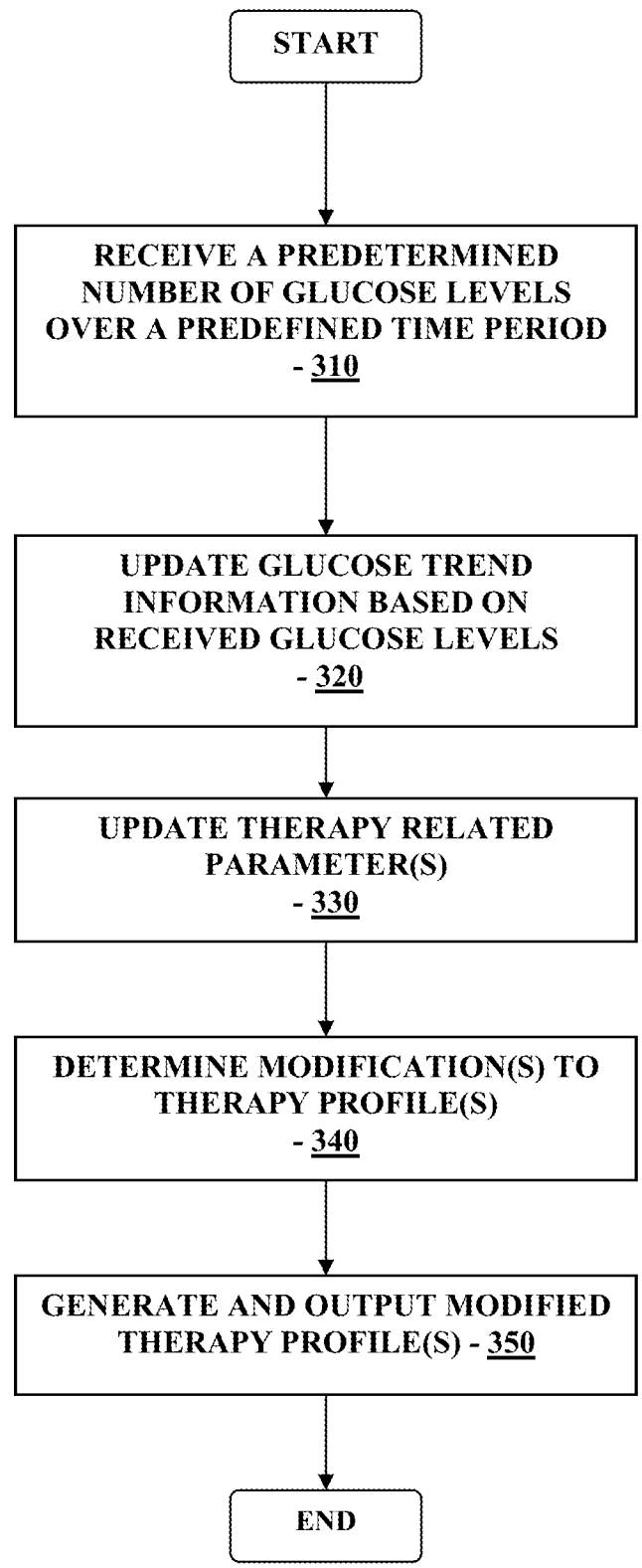
FIG. 3 is a flow chart illustrating therapy management procedure based on real time monitored analyte levels in accordance with one embodiment of the present disclosure.

FIG. 3 is a flow chart illustrating insulin therapy management procedure based on real time monitored analyte levels in accordance with one embodiment of the present disclosure. Referring to FIG. 3, in one embodiment of the present disclosure, a predetermined number of consecutive glucose levels are received or detected over a predetermined or defined time period. For example, in one embodiment, referring to FIG. 1, the monitored glucose levels of a patient is substantially continuously received or detected substantially in real time for a predetermined time period (310). In one embodiment, the predefined time period may include one or more time periods, the data within which may provide a therapeutically meaningful basis for associated data analysis.

That is, the predefined time period of the real time monitored glucose data in one embodiment may include one or more time periods sufficient to provide glucose trend information or sufficient to provide analysis of glucose levels to adjust insulin therapy on an on-going, and substantially real time basis. For example, the predefined time period in one embodiment may include one or more of a 15 minute time period, a 30 minute time period, a 45 minute time period, a one hour time period, a two hour time period and a 6 hour time period. While exemplary predefined time periods are provided herein, within the scope of the present disclosure, any suitable predefined time period may be employed as may be sufficient to be used for glucose trend determination and/or therapy related determinations (such as, for example, modification of existing basal profiles, calculation of temporary basal profile, or determination of a bolus amount).

Referring back to FIG. 3, the consecutive glucose levels received over the predefined time period in one embodiment may not be entirely consecutive due to, for example, data transmission errors and/or one or more of potential failure modes associated with data transmission or processing. As such, in one embodiment of the present disclosure, there is provided a predetermined margin of error for the received real time glucose data such that, a given number of data points associated with glucose levels which are erroneous or alternatively, not received from the glucose sensor, may be ignored or discarded.

Referring back to FIG. 3, upon receiving the predetermined number of glucose levels over a predefined time period, the glucose trend information based on the received glucose levels is updated (320). For example, in one embodiment, the glucose trend information estimating the rate of change of the glucose levels may be determined, and based upon which the projecting the level of glucose may be calculated. Indeed, in one embodiment, the glucose trend information may be configured to provide extrapolated glucose level information associated with the glucose level movement based on the real time glucose data received from the glucose sensor. That is, in one embodiment, the real time glucose levels monitored are used to determine the rate at which the glucose levels are either increasing or decreasing (or remaining substantially stable at a given level). Based on such information and over a predetermined time period, a glucose projected information may be determined.

Referring again to FIG. 3, the therapy related parameters associated with the monitored real time glucose levels are updated (330). That is, in one embodiment, one or more insulin therapy related parameters of an insulin pump such as, but not limited to, insulin on board information associated with the fluid delivery device 120 (FIG. 1), insulin sensitivity level of the patient 130 (FIG. 1), insulin to carbohydrate ratio, and insulin absorption rate. Thereafter, in one embodiment, one or more modifications to the current therapy profile are determined (340). That is, in one embodiment of the present disclosure, one or more current basal profiles, calculated bolus levels, temporary basal profiles, and/or any other suitable pre-programmed insulin delivery profiles stored in the fluid delivery device 120 (FIG. 1), for example, are retrieved and analyzed based on one or more of the received real time glucose levels, the updated glucose trend information, and the updated therapy related parameters.

Referring back to FIG. 3, after determining one or more modifications to the therapy profiles, the modified one or more therapy profiles are generated and output to the patient 130 (FIG. 1) (350) so that the patient 130 may select, store and/or ignore the one or more modified therapy profiles based on one or more of the monitored real time glucose values, updated glucose trend information, and updated therapy related parameters.

For example, in one embodiment, the patient 130 may be provided with a recommended temporary basal profile based on the monitored real time glucose levels over a predetermined time period as well as the current basal profile which is executed by the fluid delivery device 120 (FIG. 1) to deliver a predetermined level of insulin to the patient 130 (FIG. 1). Alternatively, the patient 130 in a further embodiment may be provided with one or more additional recommended actions for selection as the patient sees suitable to enhance the insulin therapy based on the real time monitored glucose levels. For example, the patient may be provided with a recommended correction bolus level based on the real time monitored glucose levels and the current basal profile in conjunction with, for example, the patient's insulin sensitivity and/or insulin on board information.

In this manner, in one embodiment of the present disclosure, based on real time monitored glucose levels, the patient may be provided with on-going, real time insulin therapy options and modifications to the pre-programmed insulin delivery basal profiles so as to improve upon the initially programmed therapy profiles based on the monitored real time glucose data.

Figure 4:
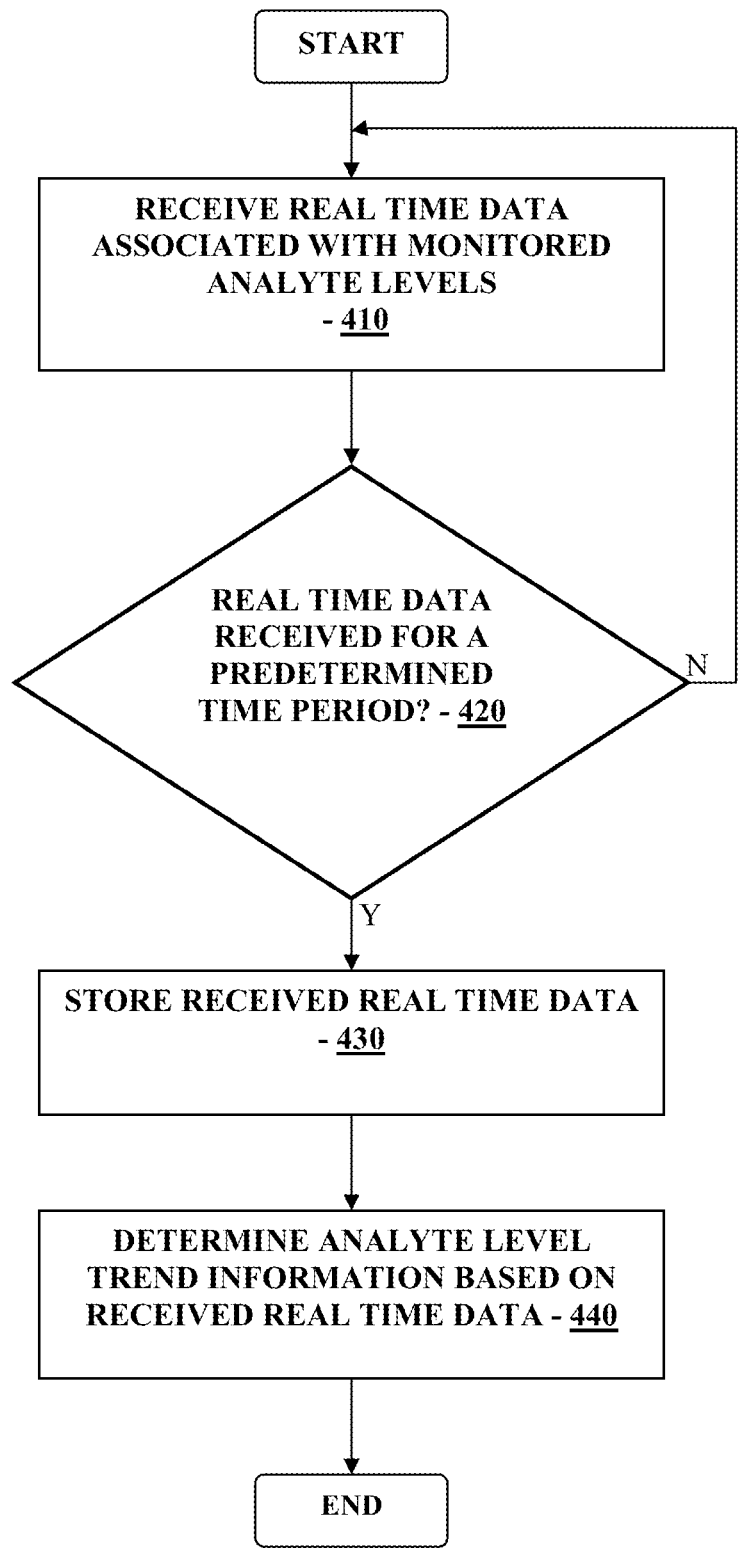
FIG. 4 is a flowchart illustrating analyte trend information updating procedure based on real time monitored analyte levels in accordance with one embodiment of the present disclosure.

FIG. 4 is a flowchart illustrating analyte trend information updating procedure based on real time monitored analyte levels in accordance with one embodiment of the present disclosure. Referring to FIG. 4, in one embodiment, real time data associated with monitored analyte levels are received (410). Thereafter it is determined whether the real time data has been received for a predetermined time period (420). If it is determined that the real time data has not been received for at least the predetermined time period, then the routine continues to receive the real time data associated with the monitored analyte levels such as glucose levels.

On the other hand, referring back to FIG. 4, if it is determined that the real time data associated with the monitored analyte levels has been received for the predetermined time period (for example, as described above in conjunction with FIG. 3), then the received real time data associated with the monitored analyte levels is stored (430). Thereafter, analyte level trend information is determined based on the received real time data associated with the monitored analyte levels (440).

For example, in one embodiment, the real time data associated with the monitored analyte levels is analyzed and an extrapolation of the data based on the rate of change of the monitored analyte levels is determined. That is, the real time data associated with the monitored analyte levels is used to determined the rate at which the monitored analyte level changed over the predetermined time period, and accordingly, a trend information is determined based on, for example, the determined rate at which the monitored analyte level changed over the predetermined time period.

In a further embodiment, the trend information based on the real time data associated with the monitored analyte levels may be dynamically modified and continuously updated based on the received real time data associated with the monitored analyte levels for one or more predetermined time periods. As such, in one embodiment, the trend information may be configured to dynamically change and be updated continuously based on the received real time data associated with the monitored analyte levels.

Figure 5:
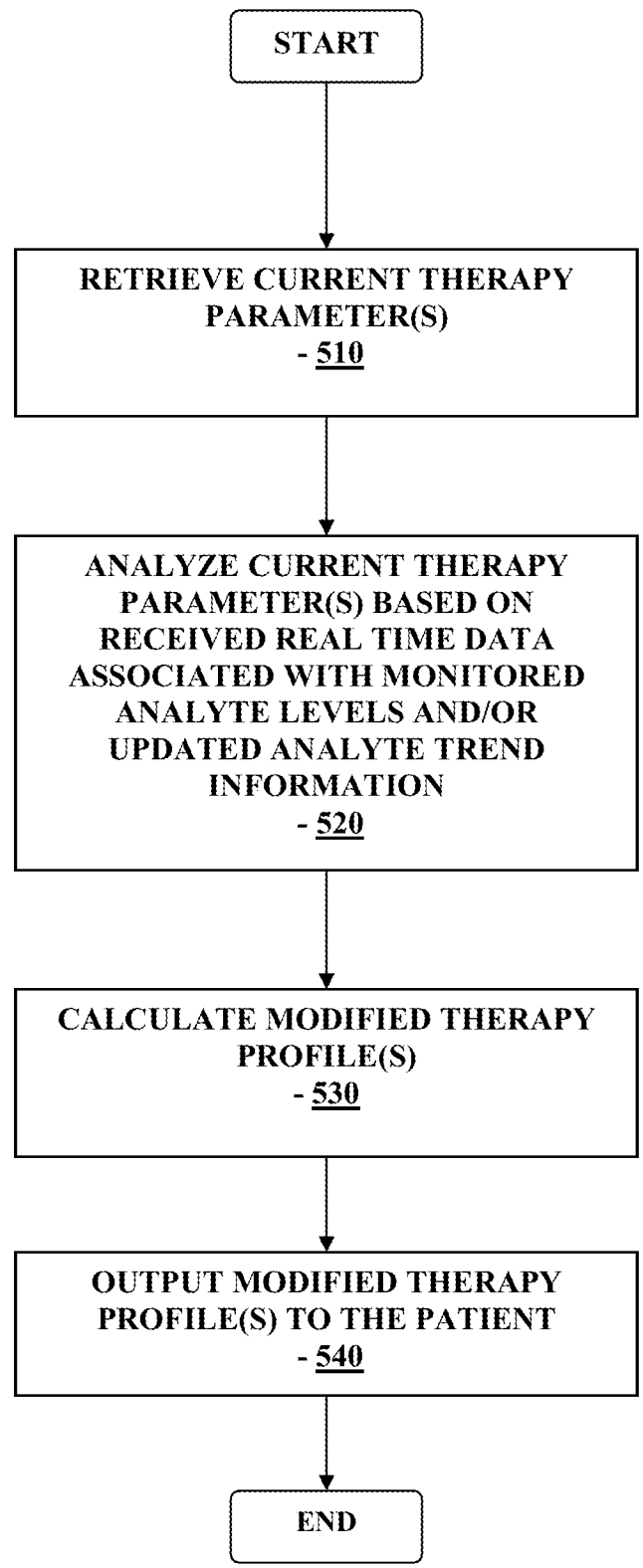
FIG. 5 is a flowchart illustrating modified therapy management procedure based on real time monitored analyte levels in accordance with one embodiment of the present disclosure.

FIG. 5 is a flowchart illustrating modified therapy management procedure based on real time monitored analyte levels in accordance with one embodiment of the present disclosure. Referring to FIG. 5, in one embodiment, the current therapy parameters are retrieved (510) and, the retrieved current therapy parameters are analyzed based on the received real time data associated with the monitored analyte levels and/or updated analyte trend information (520). For example, one or more preprogrammed basal profiles, correction bolus, carbohydrate bolus, temporary basal and associated parameters are retrieved and analyzed based on, for example, the received real time data associated with the monitored analyte levels and/or updated analyte trend information, and further, factoring in the insulin sensitivity of the patient as well as insulin on board information.

Referring to FIG. 5, based upon the analysis of the current therapy parameters, one or more modified therapy profiles are calculated (530). That is, based upon the real time glucose levels monitored by the analyte monitoring system 110 (FIG. 1), a modification or adjustment to the pre-programmed basal profiles of the fluid delivery device 120 (FIG. 1) may be determined, and the modified therapy profiles are output (540) to the patient 130 (FIG. 1). That is, the modification or adjustment to the pre-programmed basal profiles may be provided to the patient for review and/or execution to implement the recommended modification or adjustment to the pre-programmed basal profiles.

In this manner, the patient may be provided with one or more adjustments to the existing or current basal profiles or any other pre-programmed therapy profiles based on continuously monitored physiological levels of the patient such as analyte levels of the patient. Indeed, in one embodiment of the present disclosure, using continuously monitored glucose levels of the patient, modification or adjustment to the pre-programmed basal profiles may be calculated and provided to the patient for review and implementation as desired by the patient. In this manner, for example, a diabetic patient may improve the insulin therapy management and control.

Figure 6:
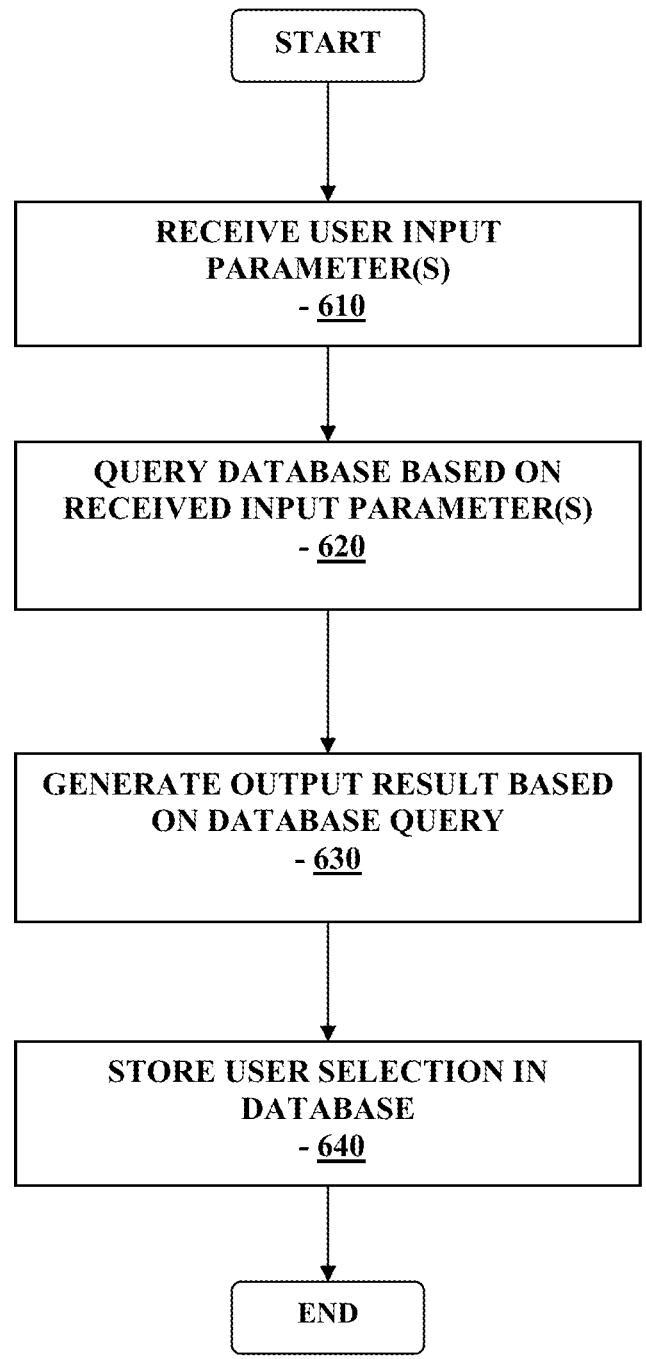
FIG. 6 is a flowchart illustrating contextual based dosage determination in accordance with one embodiment of the present disclosure.

FIG. 6 is a flowchart illustrating contextual based dosage determination in accordance with one embodiment of the present disclosure. Referring to the Figure, one or more user input parameters is received (610) such as, for example, the amount of carbohydrate to ingest, type of exercise to perform, current time of day information, or any other appropriate information that may potentially impact the determination of the suitable medication level. Based on the one or more user input parameters, one or more database is queried (620). In one embodiment, the database may be provided in the analyte monitoring system 110. Alternatively or in addition, the one or more database may be provided in the fluid delivery device 120 and/or remote terminal 140.

Referring back to FIG. 6, the database query in one embodiment may be configured to search or query for medication dosage levels that are associated with similar parameters as the received one or more user input parameters. Thereafter, the queried result is generated and provided to the user (630) which may be acted upon by the user, for example, by administering the medication dosage level based on the queried result. The user selection of the administered medication dosage level is stored in the database (640) with the associated one or more user input parameters as well as the time and date information of when the user has administered the medication dosage level.

In this manner, in one embodiment, insulin dosages and associated contextual information (e.g., user input parameters) may be stored and tracked in one or more databases. For example, a bolus amount for a diabetic patient may be determined in the manner described above using historical information without performing a mathematical calculation which takes into account variables, such as sensitivity factors that vary with time and/or user's physiological conditions, and which may need to be estimated.

In particular, in one embodiment of the present disclosure, insulin dependent users may determine their appropriate insulin dosages by, for example, using historical dosage information as well as associated physiological condition information. For example, the historical data may be stored in one or more databases to allow search or query based on one or more parameters such as the user's physiological condition and other contextual information associated with each prior bolus dosage calculated and administered. In this manner, the user may be advised on the proper amount of insulin under the particular circumstances, the user may be provided with descriptive statistical information of insulin dosages under the various conditions, and the overall system may be configured to learn and customize the dosage determination for the particular user over an extended time period.

For example, in one aspect, contextual information may be stored with the insulin bolus value. The contextual data in one aspect may include one or more of blood glucose concentration, basal rate, type of insulin, exercise information, meal information, carbohydrate content estimate, insulin on board information, and any other parameters that may be used to determine the suitable or appropriate medication dosage level. Some or all of the contextual information may be provided by the user or may be received from another device or devices in the overall therapy management system such as receiving the basal rate information from the fluid delivery device 120 (FIG. 1), or receiving the blood glucose concentration from the analyte monitoring system 110 (FIG. 1).

By way of an example, a contextually determined medication dosage level in one embodiment may be provided to the user along with a suitable or appropriate notification or message to the user that after a predetermined time period since the prior administration of the medication dosage level, the blood glucose level was still above a target level. That is, the queried result providing the suitable medication dosage level based on user input or other input parameters may be accompanied by other relevant physiological condition information associated with the administration of the prior medication dosage administration. In this manner, when the user is provided with the contextually determined medication dosage level, the user is further provided with information associated with the effects of the determined medication dosage level to the user's physiological condition (for example, one hour after the administration of the particular medication dosage level determined, the user's blood glucose level changed by a given amount). Accordingly, the user may be better able to adjust or modify, as desired or needed, the contextually determined medication dosage level to the current physiological conditions.

In this manner, in one embodiment, to determine and provide the user with proper medication dosage levels, the present or current context including the patient's current physiological condition (such as current blood glucose level, current glucose trend information, insulin on board information, the current basal profile, and so on) is considered and the database is queried for one or more medication dosage levels which correlate (for example, within a predetermined range of closeness or similarity) to the one or more current contextual information associated with the user's physiological condition, among others.

Accordingly, in one embodiment, statistical determination of the suitable medication dosage based on contextual information may be determined using, one or more of mean dosage determination, using a standard deviation or other appropriate statistical analysis of the contextual information for medication dosages which the user has administered in the past. Further, in one aspect, in the case where no close match is found in the contextual query for the desired medication dosage level, the medication dosage level with the most similar contextual information may be used to interpolate an estimated medication dosage level.

In still another aspect, the database query may be configured to provide time based weighing of prior medication dosage level determinations such that, for example, more recent dosage level determination with similar contextual information may be weighed heavier than aged dosage level determination under similar conditions. For example, older or more aged bolus amounts determined may be weighed less heavily than the more recent bolus amounts. Also, over an extended period of time, in one aspect, the older or aged bolus amounts may be aged out or weighed with a value parameter that minimally impacts the current contextual based bolus determination. In this manner, in one aspect, a highly personalized and individualistic profile for medication dosage determination may be developed and stored in the database with the corresponding contextual information associated therewith.

Figure 7:
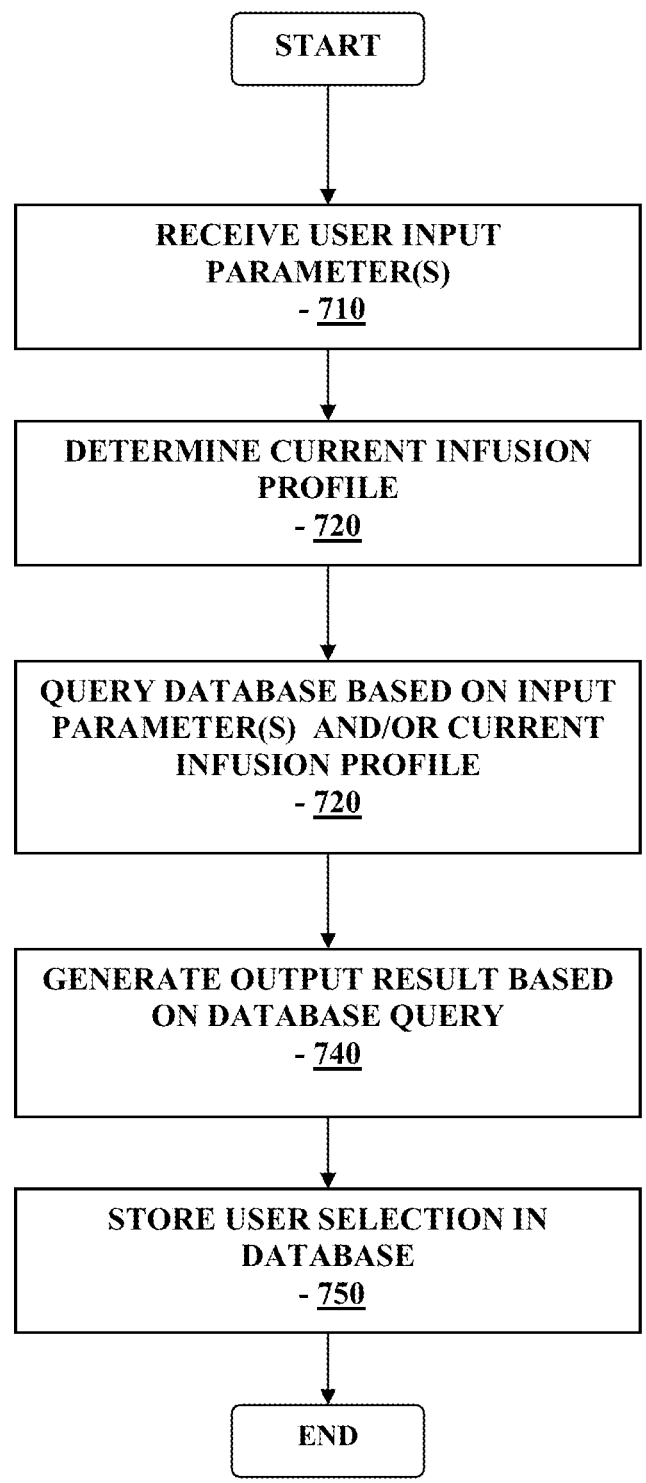
FIG. 7 is a flowchart illustrating contextual based dosage determination in accordance with one embodiment of the present disclosure.

FIG. 7 is a flowchart illustrating contextual based dosage determination in accordance with one embodiment. Referring to FIG. 7, in one aspect, when the user input parameters are received (710), the current infusion profile of the user's insulin pump is determined (720). Thereafter, the database is queried based on the input parameters and the current infusion profile (730), and which results in one or more contextually determined bolus amount associated with the input parameters and the current infusion profile (740) that is provided to the user. The determined bolus amount is then stored in the database (750) with the associated input parameters and the current infusion profile and any other contextual information associated with the determined bolus amount.

In this manner, in one aspect, in addition to the user provided input parameters, other relevant contextual information may be retrieved (for example, the current infusion profile such as basal rate from the insulin pump, the current blood glucose level and/or glucose trend information from the analyte monitoring system, and the like) prior to the database query to determine the suitable bolus amount.

As discussed above, optionally, the contextual information including the user input parameters and other relevant information may be queried to determine the suitable medication dosage level based on one or more statistical analysis such as, for example, but not limited to, descriptive statistics with the use of numerical descriptors such as mean and standard deviation, or inferential statistics including, for example, estimation or forecasting, correlation of parameters, modeling of relationships between parameters (for example, regression), as well as other modeling approaches such as time series analysis (for example, autoregressive modeling, integrated modeling and moving average modeling), data mining, and probability.

By way of a further non-limiting example, when a diabetic patient plans to administer insulin of a particular type, the patient enters contextual information such as that the patient has moderately exercised and is planning to consume a meal with a predetermined estimated carbohydrate content. The database in one embodiment may be queried for insulin dosages determined under similar circumstances in the past for the patient, and further, statistical information associated with the determined insulin dosage is provided to the user. In one aspect, the displayed statistical information associated with the determined insulin dosage may include, for example, an average amount of insulin dosage, a standard deviation or a median amount and the $25^{th}$ and the $75^{th}$ percentile values of the determined insulin dosage.

The patient may consider the displayed statistical information associated with the determined insulin dosage, and determine the most suitable or desired insulin amount based on the information received. When the patient programs the insulin pump to administer the desired insulin amount (or otherwise administer the desired insulin amount using other medication administration procedures such as injection (using a pen-type injection device or a syringe), intaking inhalable or ingestible insulin, and the like) the administered dosage level is stored in the database along with the associated contextual information and parameters.

In this manner, the database for use in the contextual based query may be continuously updated with each administration of the insulin dosage such that, each subsequent determination of appropriate insulin dosage level may be determined with more accuracy and is further customized to the physiological profile of the particular patient. Additionally, the database queried may be used for other purposes, such as, for example, but not limited to, tracking medication information, providing electronic history of the patient related medical information, and the like. Further, while the above example is provided in the context of determining an insulin level determination, within the scope of the present disclosure, other medication dosage may be determined based on the contextual based database query approaches described herein.

In a further aspect, the contextual based medication dosage query and determination may be used in conjunction with the standard or available medication dosage determination (for example, standard bolus calculation algorithms) as a supplement to provide additional information or provide a double checking ability to insure that the estimated or calculated bolus or medication dosage level is appropriate for the particular patient under the physiological condition at the time of the dosage level determination.

Within the scope of the present disclosure, the processes and routines described in conjunction with FIGS. 3-7 may be performed by the analyte monitoring system 110 (FIG. 1) and/or the fluid delivery device 120 (FIG. 1). Furthermore, the output of information associated with the context based database query for medication dosage determination may be displayed on a display unit of the receiver of the analyte monitoring system 110 (FIG. 1), or the infusion device display of the fluid delivery device 120 (FIG. 1), the display unit of the remote terminal 140 (FIG. 1), or any other suitable output device that is configured to receive the results of the database query associated with the medication dosage level determination. Alternatively, one or more such information may be output to the patient audibly as sound signal output.

In this manner, there are provided methods and system for receiving one or more parameters associated with a user physiological condition, querying a database based on the one or more parameters associated with the user physiological condition, generating a medication dosage amount based on the database query, and outputting the medication dosage amount to the user.

Optionally, statistical analysis may be performed based on the database query and factored into generating the medication dosage amount for the user.

In other aspects, there are provided methods and system for providing information associated with the direction and rate of change of analyte (e.g., glucose) levels for determination of, for example, bolus or basal rate change recommendations, for comparing expected glucose level changes to actual real time glucose level changes to update, for example, insulin sensitivity factor in an ongoing basis, and for automatically confirming the monitored glucose values within a preset time period (e.g., 30 minutes) after insulin therapy initiation to determine whether the initiated therapy is having the intended therapeutic effect.

Indeed, in accordance with the various embodiments of the present disclosure, the use of glucose trend information in insulin delivery rate determinations provides for a more accurate insulin dosing and may lead to a decrease in hypoglycemic events and improved HbA1Cs.

Accordingly, a method in one embodiment of the present disclosure includes receiving data associated with monitored analyte related levels for a predetermined time period substantially in real time, retrieving one or more therapy profiles associated with the monitored analyte related levels, generating one or more modifications to the retrieved one or more therapy profiles based on the data associated with the monitored analyte related levels.

The method may further include displaying the generated one or more modifications to the retrieved one or more therapy profiles.

In one aspect, the generated one or more modifications to the retrieved one or more therapy profiles may be displayed as one or more of an alphanumeric output display, a graphical output display, an icon display, a video output display, a color display or an illumination display.

In a further aspect, the predetermined time period may include one of a time period between 15 minutes and six hours.

The one or more therapy profiles in yet another aspect may include a basal profile, a correction bolus, a temporary basal profile, an insulin sensitivity, an insulin on board level, and an insulin absorption rate.

In still another aspect, retrieving the one or more therapy profiles associated with the monitored analyte related levels may include retrieving a current analyte rate of change information.

In yet still another aspect, generating the one or more modifications to the retrieved one or more therapy profiles may include determining a modified analyte rate of change information based on the received data associated with monitored analyte related levels.

Moreover, the method may further include generating an output alert based on the modified analyte rate of change information.

Still, the method may also include determining an analyte level projection information based on the modified analyte rate of change information.

A system for providing diabetes management in accordance with another embodiment of the present disclosure includes an interface unit, one or more processors coupled to the interface unit, memory for storing instructions which, when executed by the one or more processors, causes the one or more processors to receive data associated with monitored analyte related levels for a predetermined time period substantially in real time, retrieve one or more therapy profiles associated with the monitored analyte related levels, and generate one or more modifications to the retrieved one or more therapy profiles based on the data associated with the monitored analyte related levels.

The interface unit may include an input unit and an output unit, the input unit configured to receive the one or more analyte related data, and the output unit configured to output the one or more of the generated modifications to the retrieved one or more therapy profiles.

The interface unit and the one or more processors in a further embodiment may be operatively coupled to one or more of a housing of an infusion device or a housing of an analyte monitoring system.

The infusion device may include one of an external insulin pump, an implantable insulin pump, an on-body patch pump, a pen-type injection device, an inhalable insulin delivery system, and a transdermal insulin delivery system.

The memory in a further aspect may be configured for storing instructions which, when executed by the one or more processors, causes the one or more processors to display the generated one or more modifications to the retrieved one or more therapy profiles.

Further, the memory may be configured for storing instructions which, when executed by the one or more processors, causes the one or more processors to display the generated one or more modifications to the retrieved one or more therapy profiles as one or more of an alphanumeric output display, a graphical output display, an icon display, a video output display, a color display or an illumination display.

In one aspect, the predetermined time period may include one of a time period between 15 minutes and six hours.

The one or more therapy profiles may include a basal profile, a correction bolus, a temporary basal profile, an insulin sensitivity, an insulin on board level, and an insulin absorption rate.

In another aspect, the memory may be further configured for storing instructions which, when executed by the one or more processors, causes the one or more processors to retrieve a current analyte rate of change information.

In still another aspect, the memory may be further configured for storing instructions which, when executed by the one or more processors, causes the one or more processors to determine a modified analyte rate of change information based on the received data associated with monitored analyte related levels.

Additionally, in yet still another aspect, the memory may be further configured for storing instructions which, when executed by the one or more processors, causes the one or more processors to generate an output alert based on the modified analyte rate of change information.

Further, the memory may be further configured for storing instructions which, when executed by the one or more processors, causes the one or more processors to determine an analyte level projection information based on the modified analyte rate of change information.

A system for providing diabetes management in accordance with yet another embodiment of the present disclosure includes an analyte monitoring system configured to monitor analyte related levels of a patient substantially in real time, a medication delivery unit operatively for wirelessly receiving data associated with the monitored analyte level of the patient substantially in real time from the analyte monitoring system, a data processing unit operatively coupled to the one or more of the analyte monitoring system or the medication delivery unit, the data processing unit configured to retrieve one or more therapy profiles associated with the monitored analyte related levels, and generate one or more modifications to the retrieved one or more therapy profiles based on the data associated with the monitored analyte related levels.

In one aspect, the analyte monitoring system may be configured to wirelessly communicate with one or more of the medication delivery unit or the remote terminal such as a computer terminal (PC) or a server terminal over a radio frequency (RF) communication link, a Bluetooth® communication link, an Infrared communication link, or a wireless local area network (WLAN).

Figure 8:
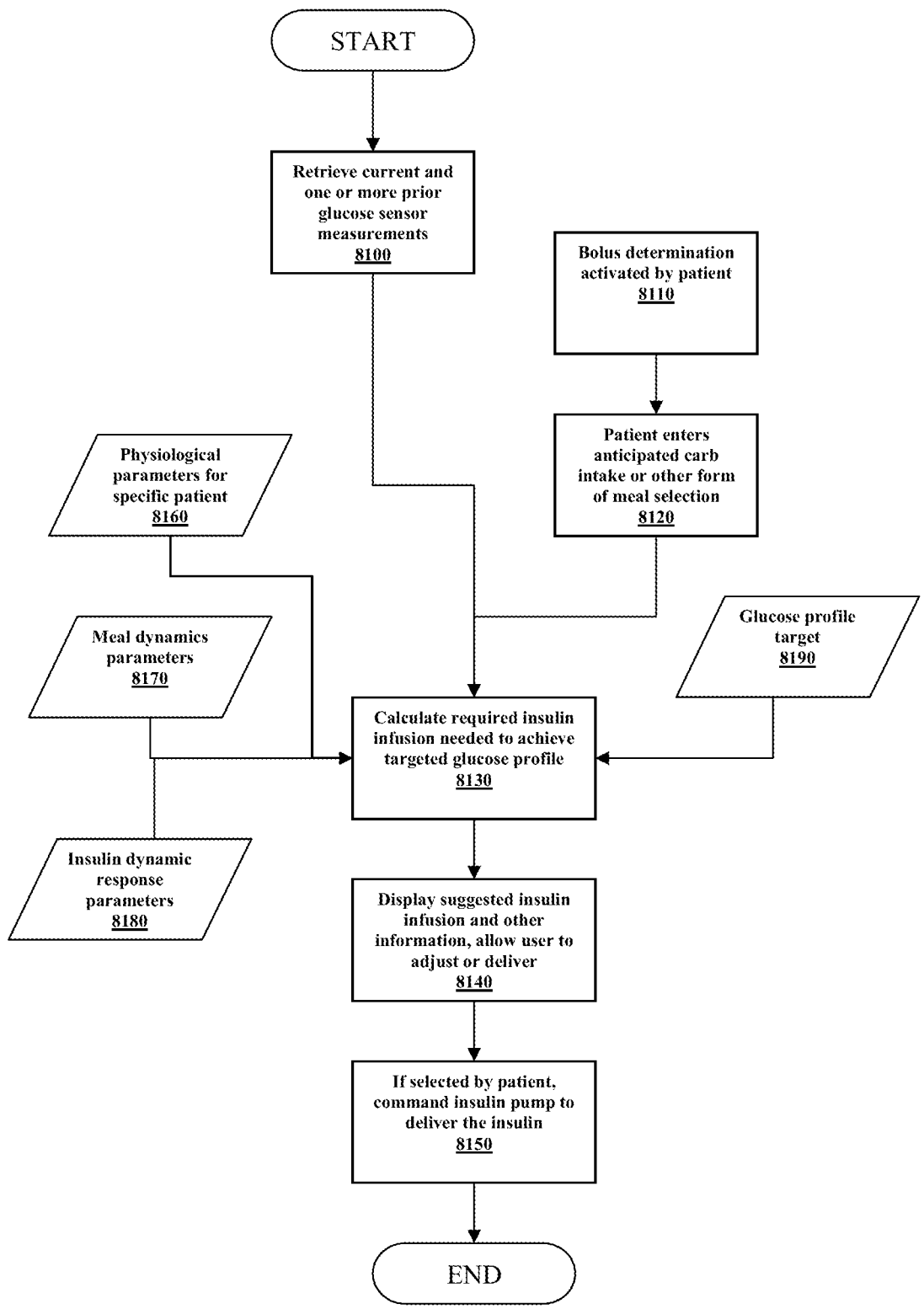
FIG. 8 illustrates dynamic medication level determination in accordance with one embodiment of the present disclosure.

FIG. 8 illustrates dynamic medication level determination in accordance with one embodiment of the present disclosure. In one aspect, the analyte monitoring system 110 (FIG. 1) may be configured to receive and store available and/or valid analyte sensor data including continuous glucose level measurement data (8100) which are indicative of the user or patient's current and past glucose levels. When the patient or the user is anticipating a meal event or any other event which may likely impact the glucose level, the patient or the user may activate or call a bolus determination function (8110) using, for example, a user interface input/output unit of the analyte monitoring system 110 (FIG. 1) or that of the fluid delivery unit 120 (FIG. 1).

Referring to FIG. 8, in one aspect the patient enters the anticipated carbohydrate intake amount, or other form of meal selection or one or more other parameters as desired for bolus determination function. With the retrieved glucose level information (8100) it is not necessary for the patient or the user to manually enter the glucose level information. In alternate embodiment, the glucose level information may be manually entered by the patient or the user. Optionally, blood glucose level may be provided to the system based on a finger stick test using a blood glucose meter device.

In one aspect, the patient or the user may enter anticipated carbohydrate information based on a pre-programmed food library stored, for example, in the analyte monitoring system 110 or the fluid delivery device 120 (FIG. 1). Such stored information may include, for example, serving size and associated carbohydrate value for different types of food, or other relevant food information related to the physiology of food update (such as fat content, for example) which may be preloaded into the analyte monitoring system 110 or the fluid delivery device 120, or alternatively, personalized by the patient or the user using custom settings and stored in the memory device of the analyte monitoring system 110 or the fluid delivery device 120.

Referring again to FIG. 8, the bolus level determination is performed in one embodiment (8110) upon patient or user activation of a user input button or component, or alternatively, in an automatic manner upon user entry of the meal information (8120). In one aspect, the bolus determination may include glucose level information from the analyte monitoring system 110 (FIG. 1) and the meal information received from the patient or the user, in conjunction with one or more of other relevant parameters described below, to propose an insulin dosage or level information to attain an anticipated blood glucose level or the future or target glucose profile (8190). In one aspect, the future or target glucose profile may be preset or alternatively, may be adjusted or modified based, for example, on the patient or user's physiological condition or profile. In one aspect, the future or target glucose profile may include a single glucose target value, or a range of desired glucose levels. Other parameters may be included in the target or future glucose profile such as, for example, maximum peak glucose value, minimum glucose value, time to achieve within 5% of the target glucose value, or other dynamic parameters. In a further aspect, the future or target glucose profile may be specified as a cost function to minimize, such as, the area defined by the accumulation in time of deviations from a target value and control sensitivity parameters, such as overshoot and undershoot. Within the scope of the present disclosure, other glucose target profiles and/or cost functions may be contemplated.

Referring back to FIG. 8, the determination of required insulin infusion to achieve the target glucose profile (8130) may include other parameters which may be predefined or patient adjustable, and/or automatically adjusted using, for example, an adaptive learning algorithm or routine that may be configured to tune the particular parameter based on a particular patient/user's physiological condition or therapy profile.

For example, one input parameter may be associated with the patient's physiological glucose response to meal intake and/or insulin intake (8160). Factors such as carbohydrate ratio and insulin sensitivity are contemplated. In one aspect, this parameter may be configured to be responsive to the various meal types or components, response time parameters and the like, such that it is updated, in real time or semi real-time, based on the change to the patient's physiological condition related to the glucose level monitored by, for example, the analyte monitoring system 110 (FIG. 1).

Another input parameter may include factors associated with the meal-meal dynamics parameters (8170). In one aspect, the meal dynamics parameters may include the timing of the meal (for example, meal event starts immediately), and the full carbohydrate intake is an impulse function—that is, the meal is substantially ingested in a short amount of time. Alternatively, factors associated with the meal dynamics parameters may be specified or programmed such as, for example, time to meal intake onset (relative to the start time of the bolus delivery), carbohydrate intake profile over time (for example, carbohydrate intake may be configured to remain substantially constant over a predetermined time period). Within the scope of the present disclosure, other elaborate intake models are contemplated.

Referring again to FIG. 8, a further input parameter may include insulin dynamic response parameters (8180) which may include physiological dynamic glucose response associated with the different types of insulin that may be delivered by, for example, fluid delivery device 120 (FIG. 1). For example, a factor associated with the insulin dynamic response parameters may include time to peak effect of the relevant insulin formulation, or a time constant associated with the glucose response which may be established by the type of insulin for delivery.

In one aspect, the calculation of the required insulin to attain the targeted glucose profile (8130) may be configured in different manners. For example, the determination may be configured as a lookup table, with input values as described above, and associated outputs of insulin profiles. In one aspect, the dynamic functional relationship that defines the physiological glucose response to the measurement inputs and parameters described above may be incorporated for determination of the desired insulin amount. The calculation or determination function may be incorporated in a regulator control algorithm that may be configured to model functional relationships and measured input values or parameters to define a control signal to drive the therapy system 100 (FIG. 1) to achieve the desired response. That is, in one aspect, the dynamic functional relationship may be defined by the physiological relationships and/or the parameter inputs. The measured input values may include the current and prior glucose values, for example, received from the analyte sensor in the analyte monitoring system 110 (FIG. 1) and the user or patient specified meal related information. The control signal discussed above may include determined or calculated insulin amount to be delivered, while the desired response includes the target or desired future glucose profile.

Referring yet again to FIG. 8, the determined insulin level, based on the calculation described above, may be displayed optionally with other relevant information, to the patient or the user (8140). In one aspect, the patient or the user may modify the determined insulin level to personalize or customize the dosage based on the user's knowledge of her own physiological conditions, for example. The patient or the user may be also provided with a function or a user input command to execute the delivery of the determined bolus amount (8150), which, upon activation, is configured to control the fluid delivery device 120 (FIG. 1) to deliver the determined amount of insulin to the patient. A further embodiment may not permit the patient modification of the determined bolus amount, and/or include automatic delivery of the determined insulin amount without patient or user intervention. In still a further embodiment, based on the monitored analyte levels of the patient, the determined insulin amount may be displayed to the user with a recommendation to defer the activation or administration of the determined insulin amount for a predetermined time period.

Figure 9:
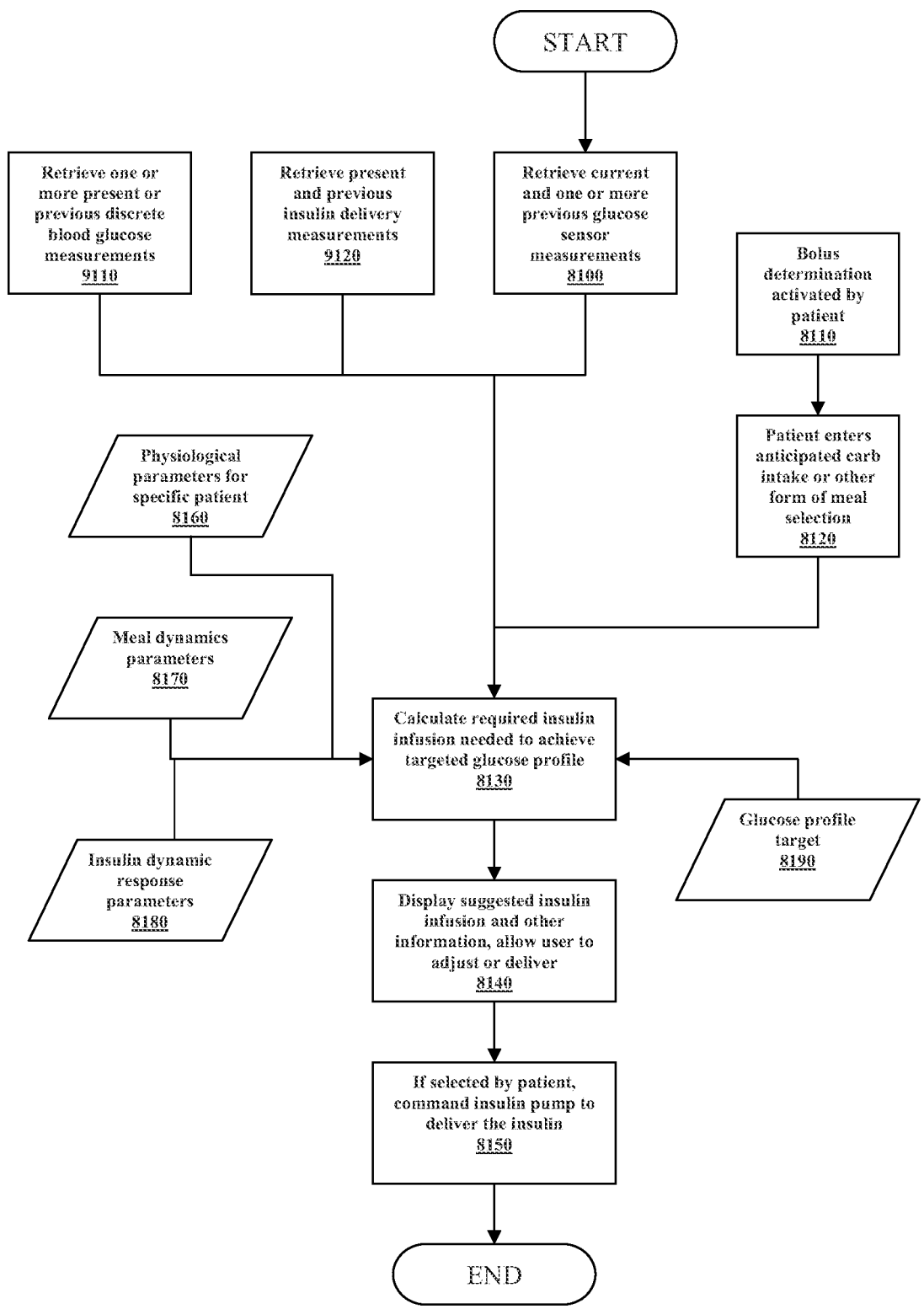
FIG. 9 illustrates dynamic medication level determination in accordance with another embodiment of the present disclosure.

FIG. 9 illustrates dynamic medication level determination in accordance with another embodiment of the present disclosure. Referring to FIG. 9, in another embodiment, the bolus determination function may include additional data from the analyte monitoring system 110 (FIG. 1), the fluid delivery device 120 (FIG. 1), and/or the remote terminal 140 (FIG. 1). More specifically, in one aspect, one or more blood glucose measurement data (9110) and/or the current and previous insulin administration profiles or measurements (9120) may be retrieved from one or more of the analyte monitoring system 110, the fluid delivery device 120 and/or the remote terminal 140 of the therapy management system 100 (FIG. 1).

Each of the measured or monitoring data or information such as analyte sensor data, blood glucose measurements, insulin delivery information and the like, in one aspect, are associated with a time stamp and stored in the one or more memory devices of the therapy management system 100. Thus, this information may be retrieved for therapy related determination such as bolus dosage calculation, or further data analysis for therapy management for the patient.

In accordance with aspects of the present disclosure, there are various sources of glucose level determination (in some instances redundant), used in several different ways. For example, Kalman filter may be used to provide for multiple measurements of the same measurable quantity. The Kalman filter may be configured to use the input parameters and/or factors discussed above, to generate an optimal estimate of the measured quantity. In a further configuration, the Kalman filter may be configured to validate the analyte sensor data based on the blood glucose measurements, where one or more sensor data may be disqualified if the blood glucose data in the relevant time period deviates from the analyte sensor data by a predetermined level or threshold. Alternatively, the blood glucose measurements may be used to validate the analyte sensor data or otherwise, calibrate the sensor data.

In a further aspect, the bolus determination function may include a subroutine to indicate unacceptable error in one or more measured data values. For example, in the case where analyte sensor data include attenuations (or "dropouts"), in one aspect, a retrospective analysis may be performed to detect the incidence of such signal attenuation in the analyte sensor data, and upon detection, the bolus determination function may be configured to ignore or invalidate this portion of data in its calculation of the desired insulin amount. Additionally, the therapy management system 100 may be configured such that insulin dosage or level calculation or determination includes a validation of analyte sensor data and/or verification of the sensor data for use in conjunction with the bolus determination (or any other therapy related determination) function.

In a further aspect of the present disclosure, various metrics may be determined to summarize a patient's monitored glucose data and related information such as, but not limited to, insulin delivery data, exercise events, meal events, and the like, to provide indication of the degree or status of the management and control of the patient's diabetic conditions. Metrics may be determined or calculated for a specified period of time (up to current time), and include, but not limited to, average glucose level, standard deviation, percentage above/below a target threshold, number of low glucose alarms, for example. The metrics may be based on elapsed time, for example, since the time of the patient's last reset of particular metric(s), or based on a fixed time period prior to the current time. Such determined metrics may be visually or otherwise provided to the patient in an easy to understand and navigate manner to provide the progression of the therapy management to the user and also, with the option to adjust or modify the related settings or parameters.

In one aspect, the output of the determined metrics may be presented to the user on the output unit 260 (FIG. 2) of the fluid delivery device 120 (FIG. 1), a display device on the analyte monitoring system 110, a user interface, and/or an output device coupled to the remote terminal 140 (FIG. 1). In one aspect, the metrics may be configured to provide a visual indication, tactile indication, audible indication or in other manner in which the patient or the user of the therapy management system 100 (FIG. 1) is informed of the condition or status related to the therapy management. Each metric may be user configurable to allow the patient or the user to obtain additional information related to the metric and associated physiological condition or the operational state of the devices used in the therapy management system 100. The metric may be associated with indicators or readings other than glucose, such as, for example, the amount and/or time of insulin delivered, percentage of bolus amount as compared to the total insulin delivered, carbohydrate intake, alarm events, analyte sensor replacement time periods, and in one aspect, the user or the patient may associate one or more alarms, alerts or notification with one or more of the metrics as may be desired.

Figure 10:
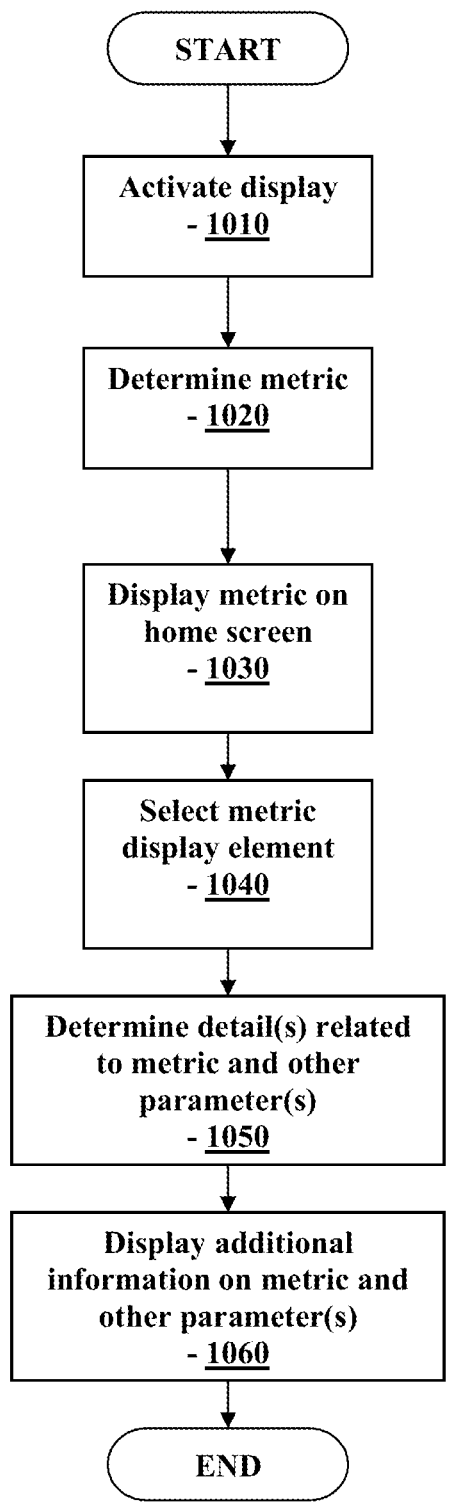
FIG. 10 illustrates metric analysis in accordance with one embodiment of the present disclosure.

FIG. 10 illustrates metric analysis in accordance with one embodiment of the present disclosure. Referring to FIG. 10, upon activation of the display (1010) or a user interface device coupled to the one or more devices in the therapy management system 100 (FIG. 1), the desired metric information is determined (1020), for example, based on the current available information (e.g., the insulin delivery information for the past 2 hours). After determining the metric information, the determined metric information is displayed on the main or home screen or display of the user interface device (1030).

In one aspect, as shown in FIG. 10, the displayed metric may be selected, for example, based on user activation on a display element (1040). Upon detecting the selection of the particular metric displayed, additional detail information related to the selected metric as well as, optionally, other related information are determined or calculated (1050), and thereafter provided to the user or the patient on the user interface device (1060). In this manner, in one aspect, the user interface device may be configured with layered menu hierarchy architecture for providing current information associated with a particular metric or condition associated with the therapy management system. The patient or the user may configure the user interface device to display or output the desired metrics at a customizable level of detail based on the particular patient or the user's settings. While the above description is provided in conjunction with a visual indication on the user interface device, within the scope of the present invention, other output indications may be similarly configured and used, such as audible notifications, vibratory or tactile notifications, and the like, each of which may be similarly configured by the patient or the user.

Within the scope of the present disclosure, the metrics may be provided on other devices that may be configured to receive periodic updates from the user interface device of the therapy management system. In one aspect, such other devices may include mobile telephones, personal digital assistants, pager devices, Blackberry® devices, remote care giver devices, remote health monitoring system or device, which may be configured for communication with the therapy management system 100, and that may be configured to process the data from the therapy management system 100 to determine and output the metrics. This may be based on real time or substantially real time data communication with the therapy management system 100. In other aspects, the therapy management system 100 may be configured to process and determine the various metrics, and transmit the determined metrics to the other devices asynchronously, or based on a polling request received from the other devices by the therapy management system 100.

The user interface device in the therapy management system 100 may be configurable such that the patient or the user may customize which metric they would like to view on the home screen (in the case of visual indication device such as a display unit). Moreover, other parameters associated with the metrics determination, such as, for example, but not limited to, the relevant time period for the particular metric, the number of metrics to be output or displayed on a screen, and the like may be configured by the user or the patient.

In a further aspect, the metric determination processing may include routines to account for device anomalies (for example, in the therapy management system 100), such as early signal attenuation (ESA) or dropouts, analyte sensor calibration, or other physiological conditions associated with the patient as well as operational condition of the devices in the therapy management system such as the fluid delivery device 120 (FIG. 1) or the analyte monitoring system 110 (FIG. 1).

Some glucose measurement anomalies may not be detected in real time and thus require retrospective detection and/or compensation. When processing a batch of current and past analyte sensor data to, for example, determine a particular metric, determine a desired bolus dosage amount, evaluate data to detect glucose control conditions, perform a data fit function to a model to execute therapy simulations, or perform any other process that may be contemplated which requires the processing of prior glucose related data, anomalies such as signal attenuation, dropouts, noise burse, calibration errors or other anomalies may be detected and/or compensated. For example, a signal dropout detector may be used to invalidate a portion of the prior glucose related data, to invalidate an entire data set, or to notify the patient or the user of the corresponding variation or uncertainly in accuracy in a predetermined one or more metrics or calculations.

Figure 11:
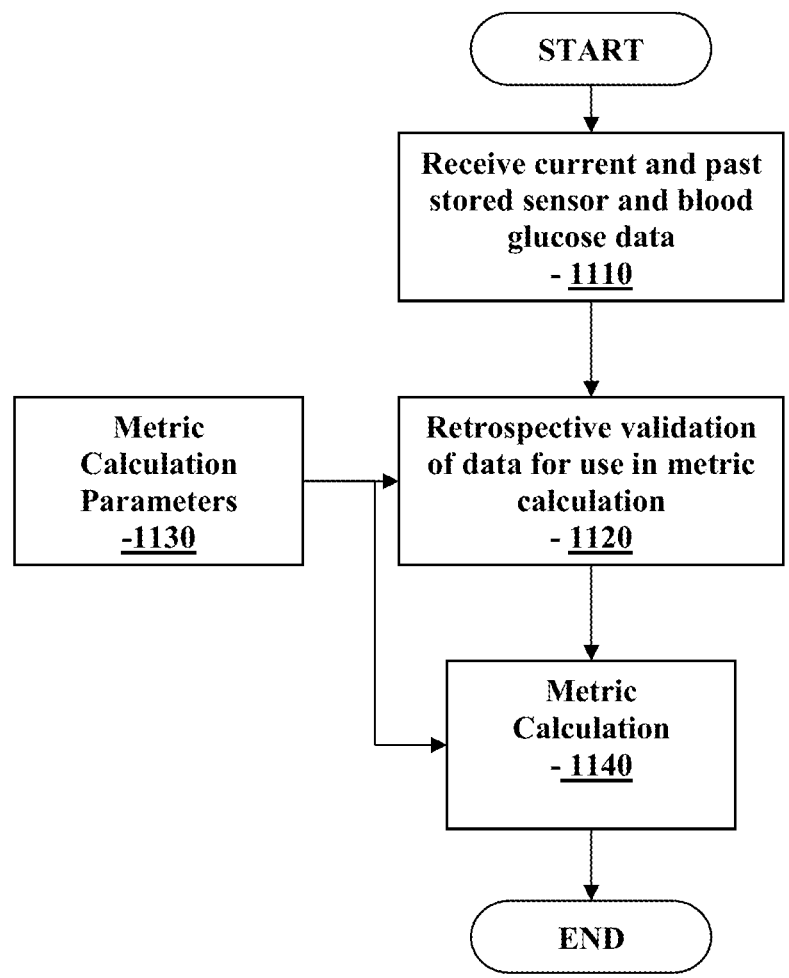
FIG. 11 illustrates metric analysis in accordance with another embodiment of the present disclosure.

For example, referring to FIG. 11 which illustrates metric analysis in accordance with another embodiment of the present disclosure, based on current and past stored sensor data and blood glucose data received (1110), retrospective validation of data used in metric calculation is performed (1120), which includes one or more metric calculation parameters (1130). Referring to FIG. 11, in one aspect, the metric calculation parameters (1130) may be used in the metric calculation (1140) which, as shown, may be performed after the data to be used in the metric calculation is retrospectively validated.

In one aspect, the metrics may be determined or recalculated after each received analyte sensor data and thereafter, displayed or provided to the user or the patient upon request, or alternatively, automatically, for example, by refreshing the display screen of the user interface device in the therapy management system 100 (FIG. 1), or otherwise providing an audible or vibratory indication to the patient or the user.

Figure 12:
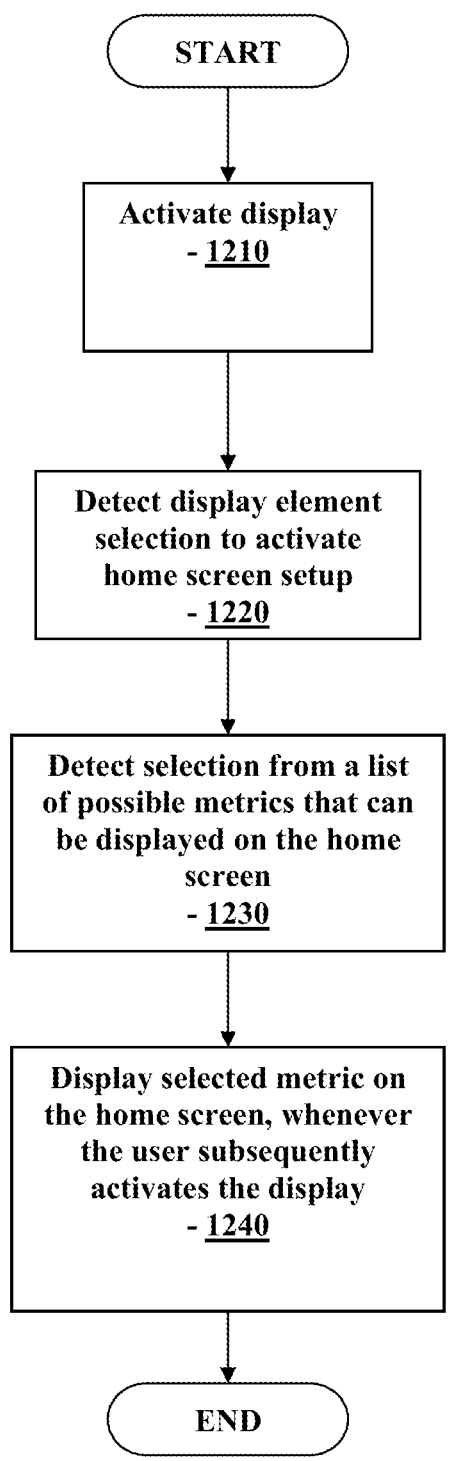
FIG. 12 is illustrates metric analysis in accordance with yet another embodiment of the present disclosure.

FIG. 12 illustrates metric analysis in accordance with yet another embodiment of the present disclosure. Referring to FIG. 12, upon detection of display activation (1210), the user interface device may be configured to activate a home screen or main menu configuration or setup function based on detected display element selection (1220). That is, in one aspect, the user or the patient may call a configuration function to customize the displayed menu associated with the display or output indication of the metrics.

Referring to FIG. 12, from the configuration menu on the user interface device, the user or patient selection of one or more metrics to be displayed or output on the main menu or home screen on the user interface device is detected (1230). After storing the user defined or selected metrics related configuration, the user interface device is configured to display or output the selected one or more metrics on the home screen or the main menu each time the user interface device is activated (1240). In this manner, in one aspect, the user or the patient may be provided with an option to display or output a particular subset of available metrics on the main display screen of the user interface device. In another aspect, the user interface device in the therapy management system 100 may be configured to include a default set of metrics to be displayed and/or updated, either in real time, or substantially in real time, or based in response to another related event such as an alarm condition, or a monitored glucose level. The system may be configured to not output any metrics.

Figure 13:
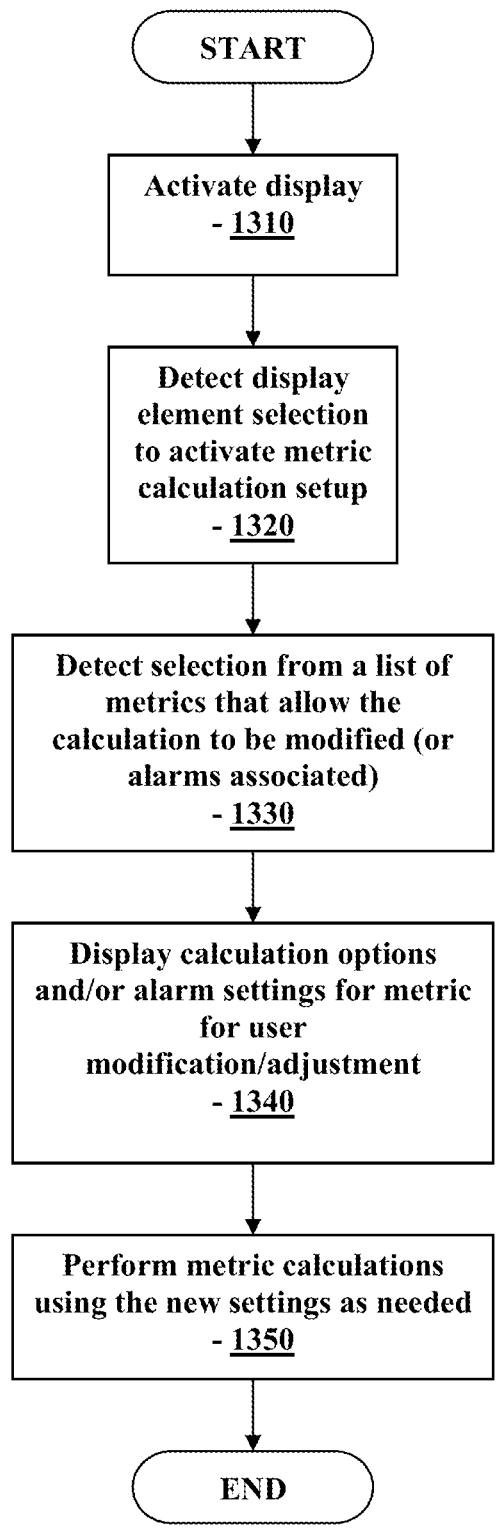
FIG. 13 illustrates metric analysis in accordance with a further embodiment of the present disclosure.

FIG. 13 illustrates metric analysis in accordance with a further embodiment of the present disclosure. Referring to FIG. 13, upon detection of the display or user interface device activation (1310), metric calculation setup function is called based on detection of a display selection to activate the same (1320), and detection of a selection from a list of metrics that allow the calculations to be modified (or alarms associated) (1330). The configuration options including metric calculation parameters, for example, are displayed (1340) in one embodiment, and the selected metric may be calculated, with one or more parameters modified or otherwise programmed, and optionally with one or more alarm conditions or settings associated with the selected metric (1350).

In this manner, the patient or the user may in one embodiment interact with the user interface device to customize or program the determination or calculation of the particular one or more metrics for display, and further, to modify the parameters associated with the calculation of the various metrics. Accordingly, in one aspect of the present disclosure, therapy related information may be configured for output to the user to, among others, provide the patient or the user of the associated physiological condition and the related therapy compliance state.

In accordance with still another aspect of the present disclosure, the therapy management system 100 (FIG. 1) may be configured to monitor potential adverse conditions related to the patient's physiological conditions. For example, a prevalence of glucose levels for a predetermined time period, pre-prandial, may be analyzed to determine if the prevalence exceeds a predefined threshold, with some consistency. Upon detection of the predefined adverse condition, the user interface device may be configured to provide a notification (visual or otherwise) to the patient or the user, and varying degrees of detailed information associated with the detected adverse condition may be provided to the patient or the user. Such notification may include text information such as, for example "Your pre-meal glucose tends to be high", or graphically by use of an arrow icon or other suitable visual indication, or a combination of text and graphics.

Adverse conditions that are not related to the monitored analyte level, such as insulin delivery data that is consistent with insulin stacking may be detected. Other examples include mean bolus event that appear to occur too late relative to the meal related glucose increases may be detected, or excessive use of temporary basal or bolus dosage or other modes of enhanced insulin delivery beyond the basal delivery profiles. Also device problems such as excessive signal dropouts from the analyte sensor may be detected and reported to the user.

In one aspect, the user interface device may be configured to customize or program the visual output indication such as icon appearance, such as enabling or disabling the icon appearance or one or more alarms associated with the detection of the adverse conditions. The notification to the user may be real time, active or passive, such that portions of the user interface device is updated to provide real time detection of the adverse conditions. Moreover, the adverse condition detection thresholds may be configured to be more or less sensitive to the triggering event, and further, parameters associated with the adverse condition detection determination may be adjusted—for example, by the time period for calculating a metric.

In a further aspect, the user interface device may provide indication of a single adverse detection condition, based on a priority list of possible adverse conditions, a list of detected adverse conditions, optionally sorted by priority, or prior detection of adverse conditions. Also, the user interface device may provide treatment recommendation related to the detected adverse condition, displayed concurrently, or options to resolve the detected adverse condition along with the detected adverse condition. In still another aspect, the notification of the detected adverse condition may be transmitted to another device, for example, that the user or the patient is carrying or using such as, for example, a mobile telephone, a pager device, a personal digital assistant, or to a remote device over a data network such as a personal computer, server terminal or the like.

In still another embodiment, some or all aspects of the adverse condition detection and analysis may be performed by a data management system, for example, by the remote terminal 140 (FIG. 1) or a server terminal coupled to the therapy management system 100. In this case, the analysis, detection and display of the adverse condition may be initiated upon the initial upload of data from the one or more analyte monitoring system 110 or the fluid delivery device 120, or both. Additionally, the adverse condition process may also account for potential measurement anomalies such as analyte sensor attenuation conditions or dropouts, or sensor calibration failures.

Figure 14:
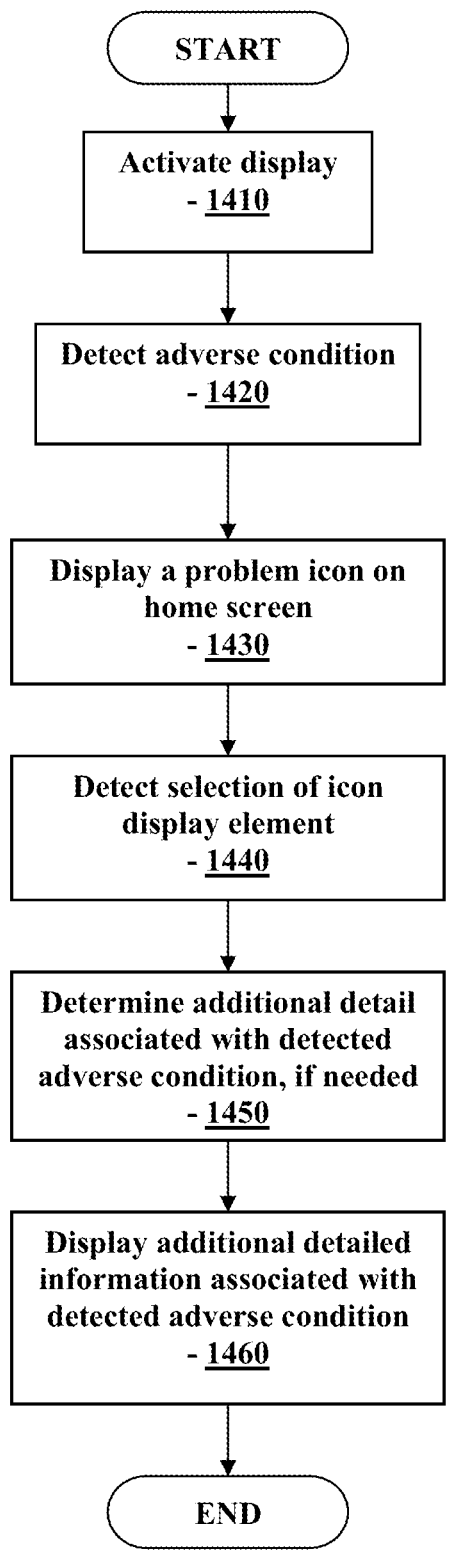
FIG. 14 illustrates condition detection or notification analysis in accordance with one embodiment of the present disclosure.

FIG. 14 illustrates condition detection or notification analysis in accordance with one embodiment of the present disclosure. Referring to FIG. 14, upon user interface device activation detection (1410) such as activation of a display device in the therapy management system 100 (FIG. 1), preprogrammed or predefined adverse condition is detected (1420), and displayed (1430) on the home screen of the user interface device using, for example, a problem icon. When the selection of the icon display element associated with the adverse condition is detected (1440), for example, indicating that the patient or the user desires additional information associated with the detected adverse condition, additional detailed information associated with the adverse condition is determined, as appropriate (1450), and thereafter, the additional detailed information is displayed to the user (1460).

Figure 15:
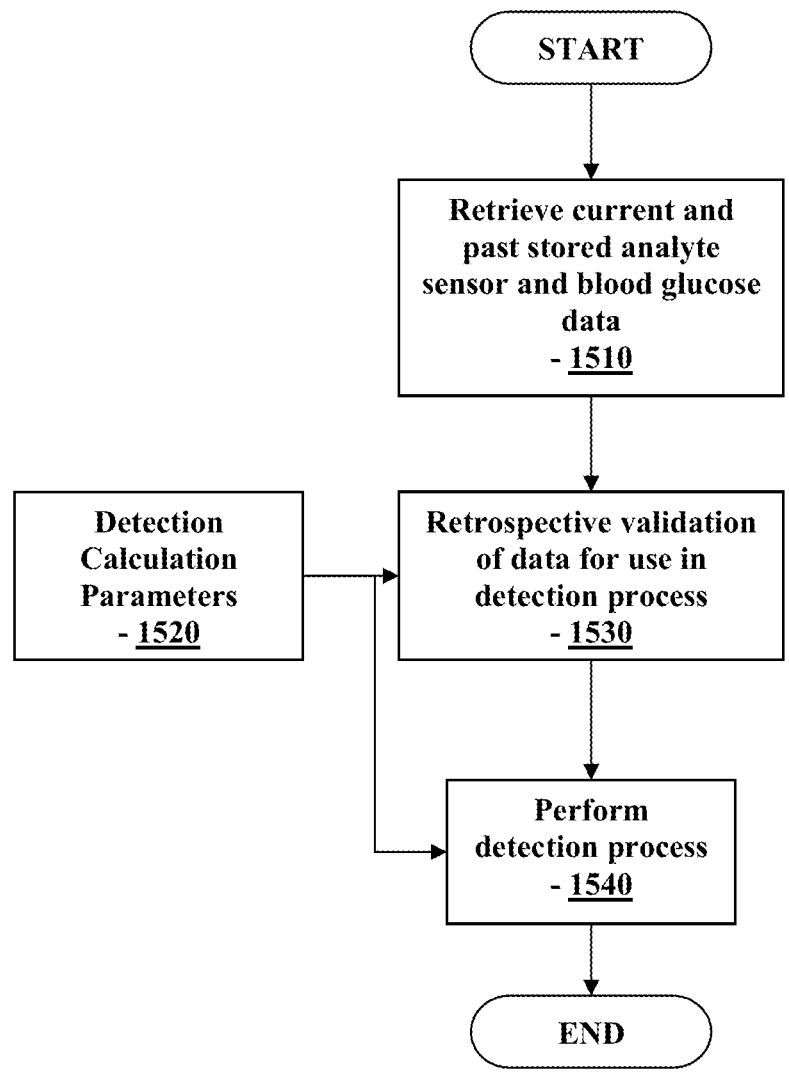
FIG. 15 illustrates condition detection or notification analysis in accordance with another embodiment of the present disclosure.

FIG. 15 illustrates condition detection or notification analysis in accordance with another embodiment of the present disclosure. Referring to FIG. 15, current and prior stored analyte sensor data and blood glucose data are retrieved (1510) and retrospective validation of the data for use in the adverse condition detection process is performed (1530), based also, at least in part, on the detection calculation parameters (1520) which may be user input or preprogrammed and stored. Thereafter, the adverse condition detection process is performed (1540), for example, the parameters associated with the programmed adverse conditions are monitored and upon detection, notified to the patient or the user.

Figure 16:
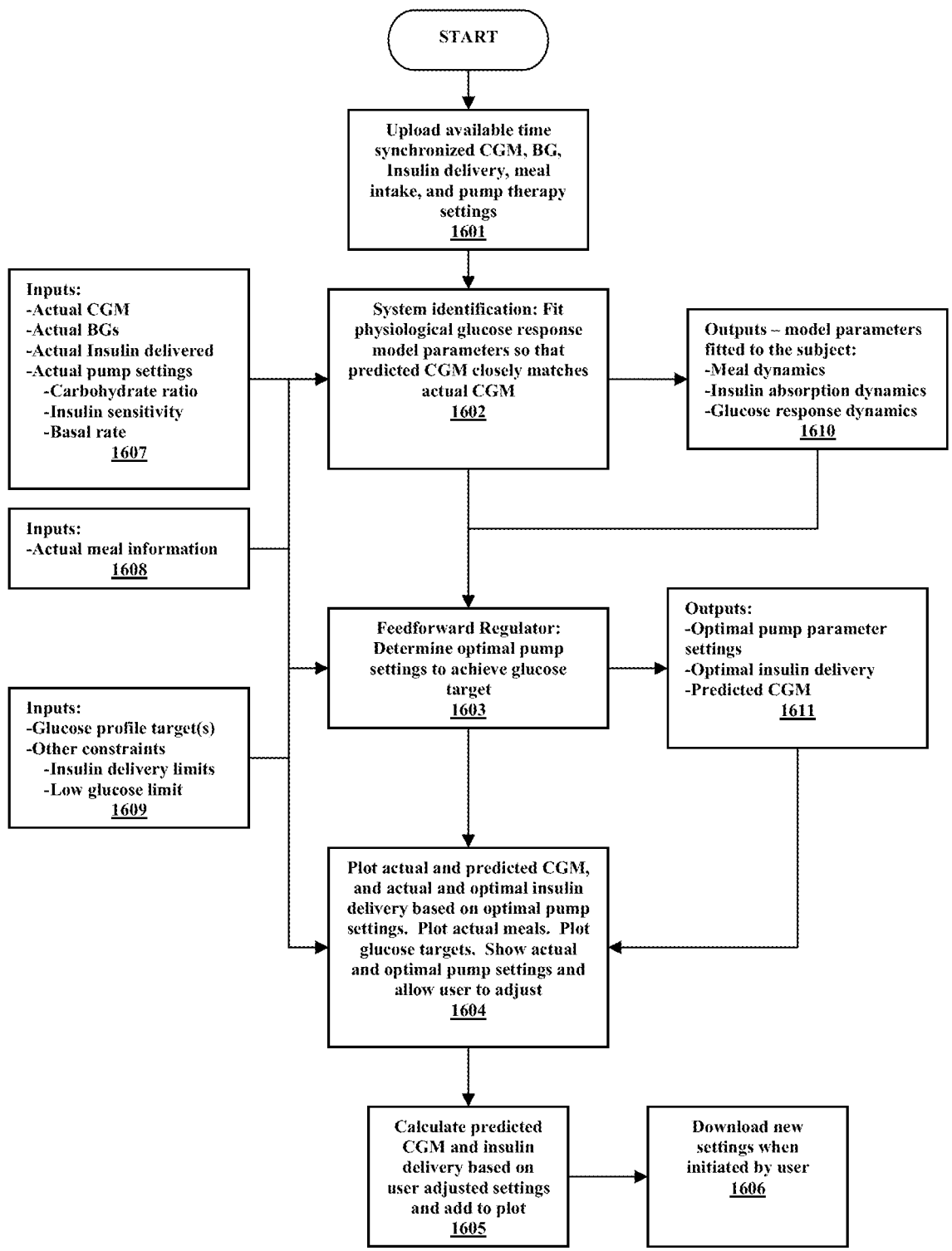
FIG. 16 illustrates therapy parameter analysis in accordance with one embodiment of the present disclosure.

In accordance with yet a further aspect of the present disclosure, therapy analysis system is provided. In one aspect, the therapy management system 100 (FIG. 1) may be used to collect and store patient related data for analysis to optimize therapy profiles and associated parameters for providing treatment to the patients. More specifically, FIG. 16 illustrates therapy parameter analysis in accordance with one embodiment of the present disclosure. As shown, data from a continuous glucose monitoring system (CGM) such as an analyte monitoring system 110 (FIG. 1) and an insulin pump such as, for example, fluid delivery device 120 (FIG. 1) are collected or stored over a predetermined time period. In addition, during this time period, meal intake information may be stored, along with other relevant data such as, exercise information, and other health related information. All data is stored with a corresponding date and time stamp and are synchronized.

After the predetermined time period, the stored data including, for example, time synchronized analyte sensor data (CGM), blood glucose (BG) data, insulin delivery information, meal intake information and pump therapy settings, among others, are uploaded to a personal computer, for example, such as the remote terminal 140 (FIG. 1) for further analysis (1601). The received data is used as input data including, for example, actual glucose data (CGM), actual blood glucose data (BG), actual insulin amount delivered, actual pump settings including carbohydrate ratio, insulin sensitivity, and basal rate, among others (1607), as well as actual meal information (1608), to perform a system identification process (1602).

More specifically, the system identification process (1602) in one embodiment is configured to fit the received input data to a generic physiological model that dynamically describes the interrelationship between the glucose levels and the delivered insulin level as well as meal intake. In this manner, in one aspect, the system identification process (1602) is configured to predict or determine glucose levels that closely matches the actual glucose level (CGM) received as one of the input parameters.

Referring to FIG. 16, as shown, the parameters of the generic physiological model are adjusted so that the model output (glucose level) closely matches the actual monitored glucose level when the measured inputs are applied (1610). That is, a newly identified model is generated based, at least in part, on meal dynamics, insulin absorption dynamics, and glucose response dynamics. Thereafter, based on the newly identified model (1610), actual meal information representing carbohydrate intake data (1608), and the glucose profile target(s) as well as any other constraints such as insulin delivery limits, low glucose limits, for example (1609), to determine the optimal pump setting to obtain the target glucose profile(s) (1603). That is, in one aspect, based on a predefined cost function such as minimizing the area about a preferred glucose level, or some other boundaries, predicted glucose levels are determined based on optimal pump therapy settings, and optimal insulin delivery information (1611).

Based on the analysis performed as described above, a report may be generated which shows model day results, with median and quartile traces, and illustrating the actual glucose levels and glucose levels predicted based on the identified model parameters, actual insulin delivery information and optimal insulin delivery information, actual mean intake information, and actual and optimal insulin therapy settings (1604). Other report types can be generated as desired. In one aspect, a physician or a treatment provider may modify one or more parameters to view a corresponding change in the predicted glucose values, for example, that may be more conservative to reduce the possibility of hypoglycemia.

Referring again to FIG. 16, a new predicted glucose and insulin delivery information based on the adjusted setting are determined (1605). The predicted glucose values and insulin delivery information are added to the plot displayed and in one aspect, configured to dynamically change, in real time, in response to the parameter adjustments. Upon determination of an acceptable therapy profile, the settings and/or parameters associated with the insulin delivery, including, for example, modified basal profiles, for the insulin pump, may be downloaded (1606) to the pump controller from the computer terminal (for example, the remote terminal 140) for execution by the insulin pump, for example, the fluid delivery device 120 (FIG. 1).

Figure 17:
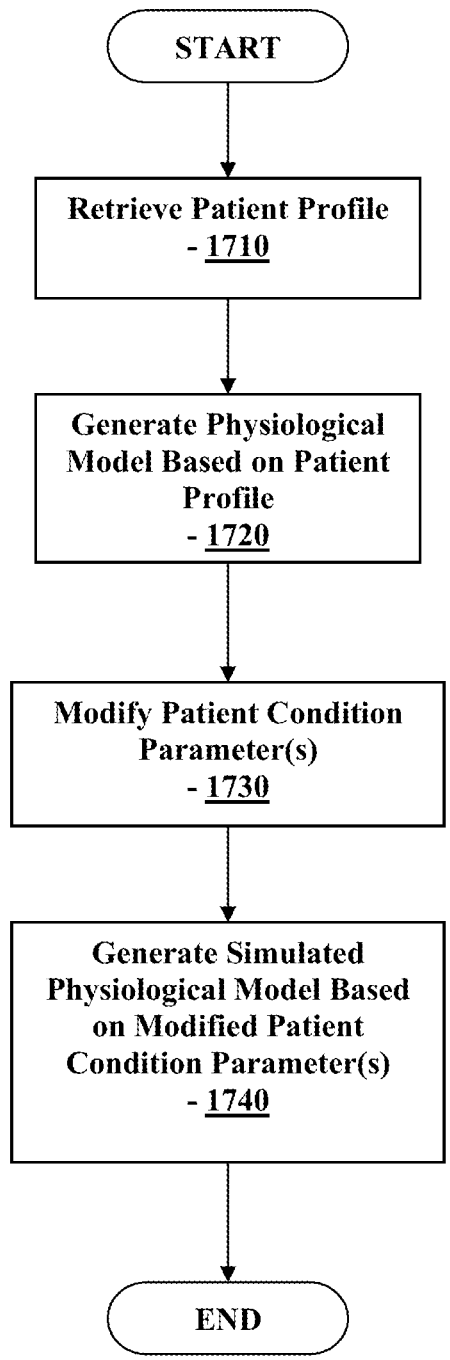
FIG. 17 is a flowchart illustrating dynamic physiological profile simulation routine in accordance with one embodiment of the present disclosure.

FIG. 17 is a flowchart illustrating a dynamic physiological profile simulation routine in accordance with one embodiment of the present disclosure. Referring to FIG. 17, in one aspect of the present disclosure, the physiological profile of a patient or user based on data collected or received from one or more of the analyte monitoring system 110 (FIG. 1) or the fluid delivery device (120) for example, are retrieved (1710). For example, based on a collection of data associated with monitored analyte levels of a patient and/or the therapy information such as the actual or programmed insulin delivery profiles, the profile of a patient which represents the physiological condition of the patient is retrieved. Other relevant data could be collected, for example, but not limited to, the patient's physical activities, meal consumption information including the particular content of the consumed meal, medication intake including programmed and executed basal and/or bolus profiles, other medication ingested during the relevant time period of interest.

Thereafter, a simulation of a physiological model based on the retrieved physiological condition is generated (1720). In one aspect, the generated physiological model includes one or more parameters associated with the patient's physiological condition including, for example, insulin sensitivity, carbohydrate ratio and basal insulin needs. In one aspect, the relevant time period of interest for physiological simulation may be selected by the patient, physician or the care provider as may be desired. In one aspect, there may be a threshold time period which is necessary to generate the physiological model, and thus a selection of a time period shorter than the threshold time period may not result in accurate physiological modeling. For example, in one aspect, the data processing system or device may be configured to establish a seven day period as the minimum number of days based on which, the physiological modeling may be achieved.

Referring to FIG. 17, with the generated physiological model based on the patient's profile, one or more patient condition parameters may be modified (1730). For example, the basal profile for the infusion device of the patient may be modified and entered into the simulation module. Alternatively or in addition, the patient's profile may be modified. For example, the type or amount of food to be ingested may be provided into the simulation module. Within the scope of the present disclosure, the patient, the physician or the care provider may modify one or more of the condition parameters to determine the simulated effect of the modified condition parameter or profile component to the physiological model generated. More specifically, referring back to FIG. 17, when one or more patient condition parameters or one or more profile components is modified, the simulated physiological model is modified or altered in response to the modified condition parameter(s) (1740).

That is, in one aspect, the simulation of the initial physiological profile of a patient may be generated based on collected/monitored data. Thereafter, one or more parameters may be modified to show the resulting effect of such modified one or more patient condition parameters on the simulation of the patient's physiological model. In this manner, in one aspect, the patient, physician or the healthcare provider may be provided with a simulation tool to assist in the therapy management of the patient, where a model based on the patient's condition is first built, and thereafter, with adjustment or modification of one or more parameters, the simulation model provides the resulting effect of the adjustment or modification so as to allow the patient, physician or the healthcare provider to take appropriate actions to improve the therapy management of the patient's physiological condition.

Figure 18:
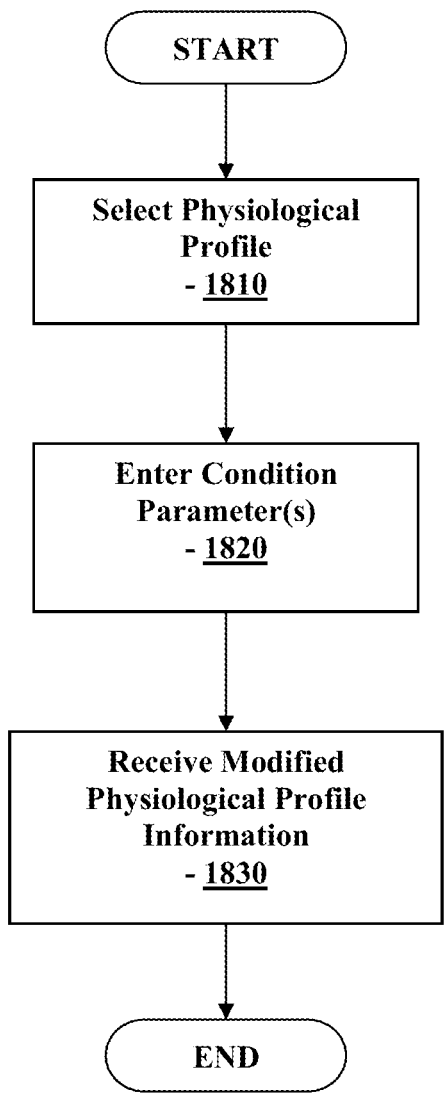
FIG. 18 is a flowchart illustrating dynamic physiological profile simulation routine in accordance with another embodiment of the present disclosure.

FIG. 18 is a flowchart illustrating a dynamic physiological profile simulation routine in accordance with another embodiment of the present disclosure. Referring to FIG. 18, in another embodiment, a user selects, using one or more user input devices of a personal computer or other computing or data processing device, the desired physiological profile (1810), and thereafter, one or more condition parameters displayed to the user may be selected as desired. For example, the user may be prompted to select an insulin level adjustment setting, to view a simulation of the physiological profile model responding to such insulin level adjustment setting.

In another aspect, the user may select an activity adjustment setting to view the effect of the selected activity on the physiological profile model. For example, the user may select to exercise for 30 minutes before dinner every day. With this adjustment to the condition parameter, the physiological profile model simulation module may be configured to modify the generated physiological model to show the resulting effect of the exercise on the glucose level of the patient in view of the existing insulin delivery profile, for example. In this manner, one or more parameters associated with the patient's physiological condition may be modified as a condition parameter and provided to the model simulation module to determine the resulting effect of such modified condition parameter (1820). Indeed, referring back to FIG. 18, with the entered condition parameter(s) selected by the patient, physician or the healthcare provider, the simulation module in one aspect may be configured to generate a modified physiological profile model which is received or output to the user, patient, physician or the healthcare provider, visually, graphically, in text form, or one or more combinations thereof (1830).

Figure 19:
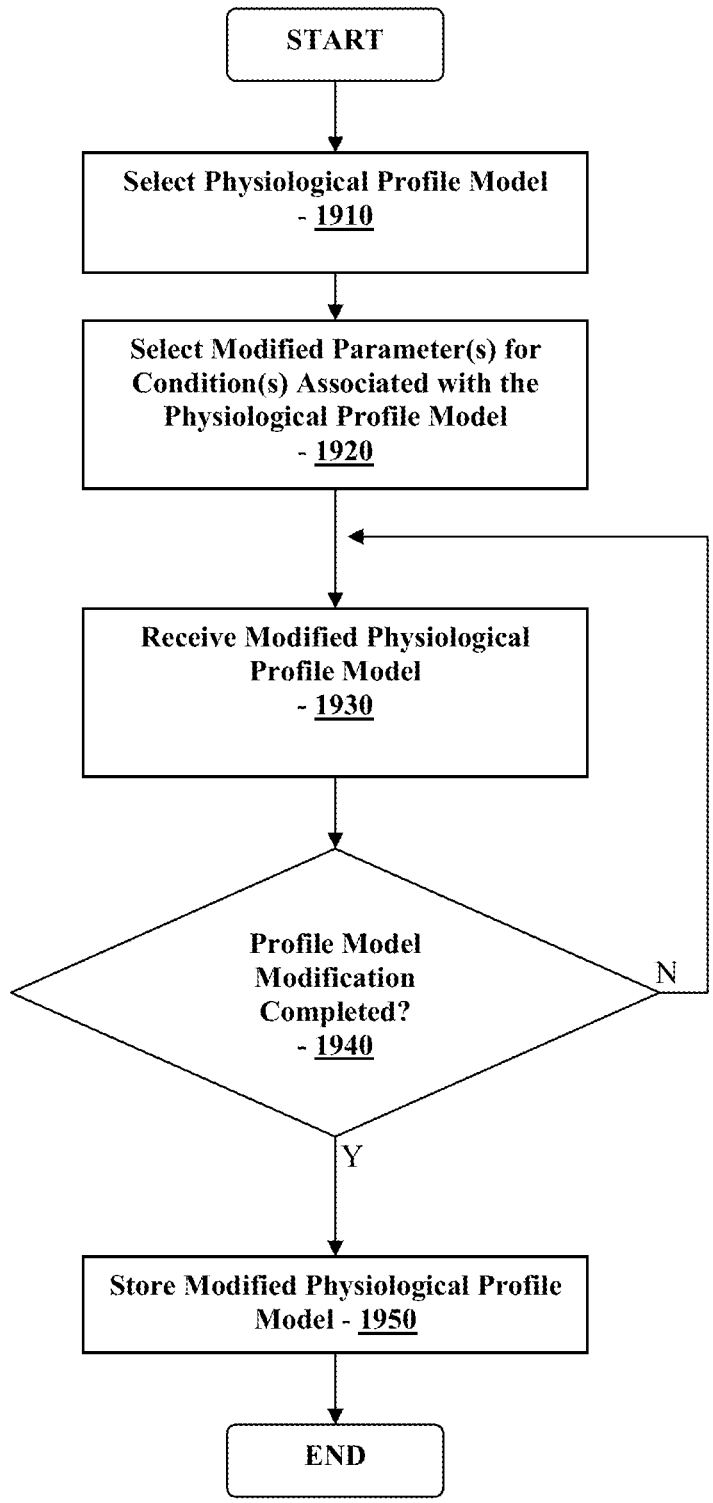
FIG. 19 is a flowchart illustrating dynamic physiological profile simulation routine in accordance with still another embodiment of the present disclosure.

FIG. 19 is a flowchart illustrating dynamic physiological profile simulation routine in accordance with still another embodiment of the present disclosure. Referring to FIG. 19, in one aspect, when the physiological profile model is selected (1910) and the desired modified parameter(s) is selected for the condition(s) associated with the physiological profile model (1920), a modified physiological model is received (1930) or output to the user on a display device of the data processing terminal or computer. Thereafter, the simulation module may prompt the patient, the user, physician or the healthcare provider to either enter additional or different condition parameters to view the resulting effect on the simulated physiological model, or alternatively, select the option to indicate the completion of the modification to the condition parameters (1940).

In this manner, an iteration may be provided such that the patient, user, physician or the healthcare provider may modify one or more conditions associated with the patient's physiological condition, and in response, view or receive in real time, the resulting effect of the modified one or more conditions to the modeled physiological condition simulation. Thereafter, optionally, the modified as well as the initial physiological profile model (and including any intermediate modification to the physiological profile model based on one or more parameter inputs) may be stored in the memory or storage unit of the data processing terminal or computer (1950).

In this manner, in one aspect, when the simulation module has sufficient data associated with the patient's physiological condition or state to define the simulation model parameters, the patient, healthcare provider, physician or the user may model different treatment scenarios to determine strategies for managing the patient's condition such as the diabetic condition in an interactive manner, for example. Thus, changes to the resulting physiological model may be displayed or provided to the patient, physician or the healthcare provider based on one or more potential changes to the treatment regimen.

Figure 20:
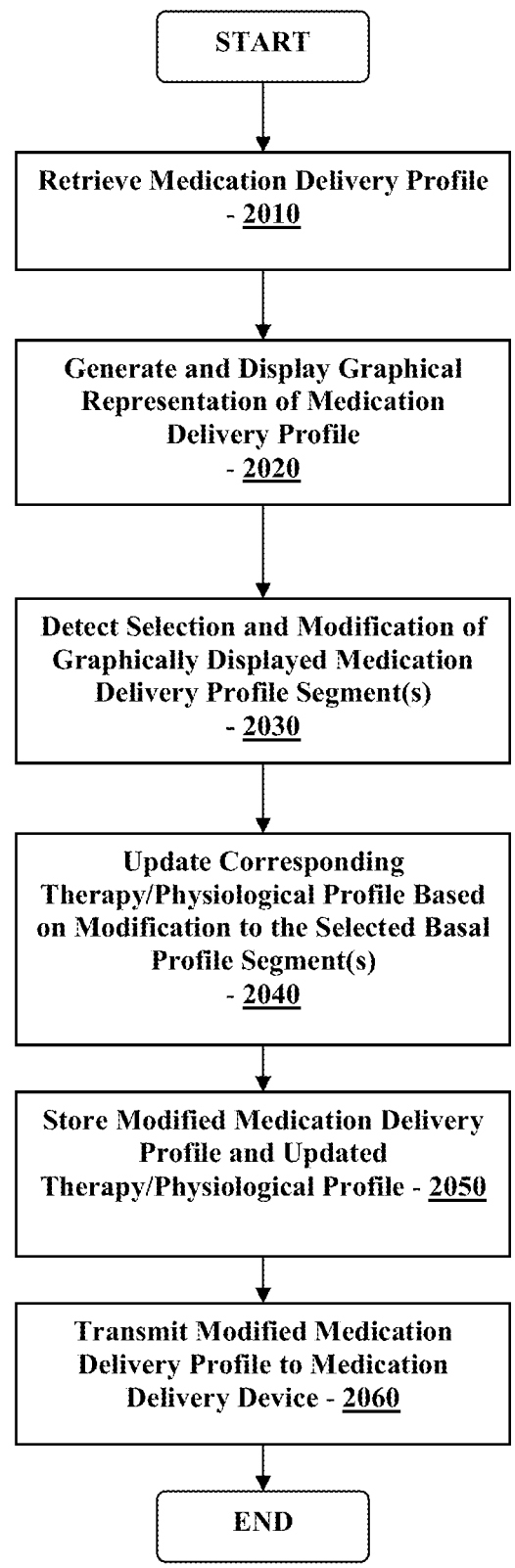
FIG. 20 is a flowchart illustrating visual medication delivery profile programming in accordance with one embodiment of the present disclosure.

FIG. 20 is a flowchart illustrating visual medication delivery profile programming in accordance with one embodiment of the present disclosure. Referring to FIG. 20, medication delivery profile such as a basal rate profile is retrieved (2010), for example, from memory of the remote terminal 140 (FIG. 1) or received from the fluid delivery device 120 (FIG. 1) such as an insulin pump. Thereafter, a graphical representation of the medication delivery profile is generated and displayed (2020) on the display unit of the remote terminal 140. For example, the graphical representation of the medication delivery profile may include a line graph of the insulin level over a predetermined time period for the corresponding medication delivery profile.

In one aspect, the graphically displayed medication delivery profile may be configured to be manipulated using an input device for the remote terminal 140 such as, for example, a computer mouse, a pen type pointing device, or any other types of user input device that is configured for manipulation of the displayed objects on the display unit of the remote terminal 140. In addition to the graphical display of the medication delivery profile, one or more of a corresponding therapy or physiological profile for a particular patient or user may be displayed. For example, in one embodiment, based on data received from the analyte monitoring system 110 and/or the fluid delivery device 120, the remote terminal 140 may be configured to display the basal profile programmed in the fluid delivery device 120 indicating the amount of insulin that has been programmed to administer to the patient, and the corresponding monitored analyte level of the patient, insulin sensitivity, insulin to carbohydrate ratio, and any other therapy or physiological related parameters.

Referring to FIG. 20, the patient or the user including a physician or the healthcare provider may manipulate the user input device such as the computer mouse coupled to the remote terminal 140 to select and modify one or more segments of the graphically displayed medication delivery profile (2030). In response to the display manipulation/modification, the corresponding displayed therapy/physiological profile may be dynamically updated (2040). For example, using one or more of the user input devices, the user or the patient may select a portion or segment of the basal profile line graph, and either move the selected portion or segment of the line graph in vertical or horizontal direction (or at an angle), to correspondingly modify the level of the medication segment for a given time period as graphically displayed by the line graph.

In one aspect, the medication delivery profile in one aspect may be displayed as a line graph with time of day represented along the X-axis and the value or level of the medication on the Y-axis. When the computer mouse is moved near a segment of the line graph, the cursor displayed on the remote terminal 140 display unit may be configured to change to indicate that the portion of the line graph may be selected and dragged on the displayed screen. For example, the horizontal portions of the line graph may be dragged in a vertical direction to increase or decrease the setting or the medication level for that selected time period, while the vertical portions of the line graph may be dragged in the horizontal direction to adjust the time associated with the particular medication level selected.

Referring again to FIG. 20, in one aspect, the modified medication delivery profile and the updated therapy/physiological profile are stored (2050) in a storage unit such as a memory of the remote terminal 140, and thereafter, may be transmitted to one or more of the fluid delivery device 120 or the analyte monitoring system 110 (2060). In this manner, in one aspect, the patient or the user may be provided with an intuitive and graphical therapy management tool which allows manipulation of one or more parameters associated with the patient's condition such as diabetes, and receive real time visual feedback based on the manipulation of the one or more parameters to determine the appropriate therapy regimen.

For example, when the user or the patient wishes to maintain his or her blood glucose level within a predetermined range, the user may manipulate the line graph associated with the insulin delivery rate, for example, to receive feedback on the effect of the change to the insulin amount on the blood glucose level. The modeling of the physiological parameters associated with the patient in one aspect may be generated using computer algorithms that provide simulated model of the patient's physiological condition based on the monitored physiological condition, medication delivery rate, patient specific conditions such as exercise and meal events (and the types of exercise and meal for the particular times), which may be stored and later retrieved for constructing or modeling the patient's physiological conditions.

Figure 21:
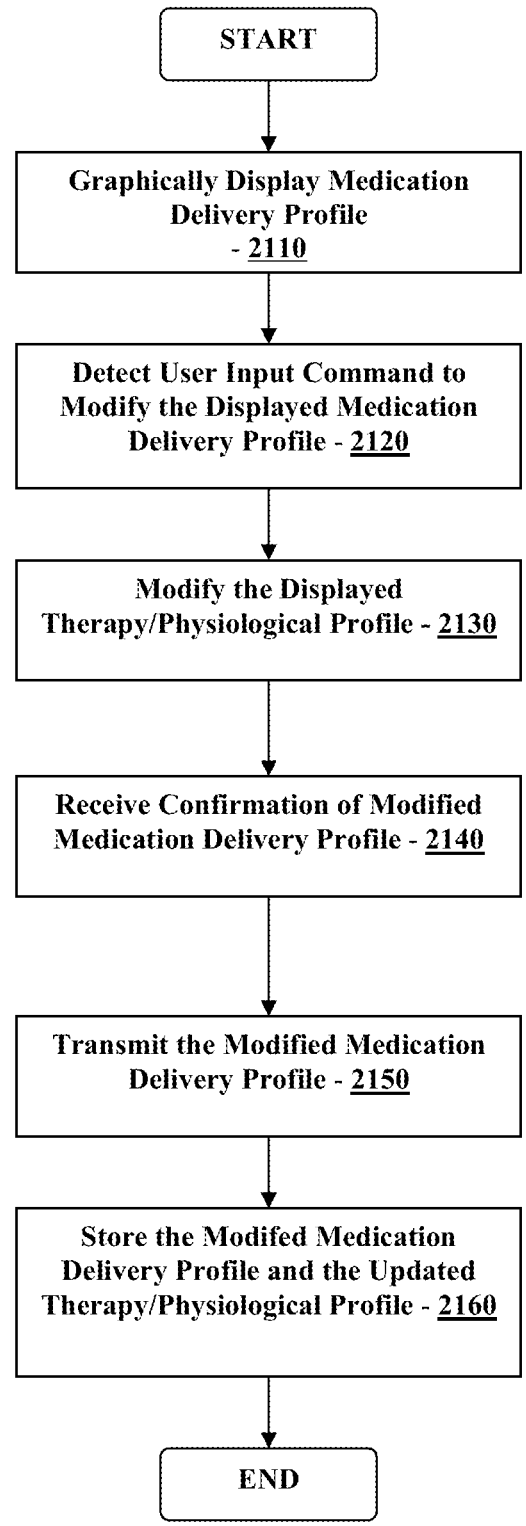
FIG. 21 is a flowchart illustrating visual medication delivery profile programming in accordance with another embodiment of the present disclosure.

FIG. 21 is a flowchart illustrating visual medication delivery profile programming in accordance with another embodiment of the present disclosure. Referring to FIG. 21, medication delivery profile for a particular patient may be graphically displayed (2110), and thereafter, upon detection of an input command to modify the displayed medication delivery profile (2120), the corresponding displayed therapy physiological profile is modified (2130). As discussed above, the input command may be received from an input device such as a computer mouse executing select and drag functions, for example, on the display screen of the remote terminal 140. In one aspect, in response to the input command, the displayed medication delivery profile as well as the corresponding displayed therapy/physiological profile may be graphically updated to provide visual feedback to the patient or the user of the effect resulting from the input command modifying the medication delivery profile.

Referring to FIG. 21, when the confirmation of the modified medication delivery profile is received (2140), for example, via the user input device, the modified medication delivery profile may be transmitted (2150) and, the modified medication delivery profile and the updated therapy/physiological profile are stored (2160). That is, when the user or the patient confirms or accepts the modification or update to the medication delivery profile based, for example, on the visual feedback received corresponding to the change to the therapy/physiological profile, in one aspect, the modified medication delivery profile may be transmitted to the fluid delivery device 120 to program the device for execution, for example. The transmission may be wireless using RF communication, infrared communication or any other suitable wireless communication techniques, or alternatively, may include cabled connection using, for example, USB or serial connection.

In this manner, in one aspect, there is provided an intuitive and easy to use visual feedback mechanism to improve treatment of a medical condition such as diabetes, by providing visual modeling of the therapy regimen that can be dynamically adjusted to show the effect of such adjustment to the physiological condition.

Figure 22:
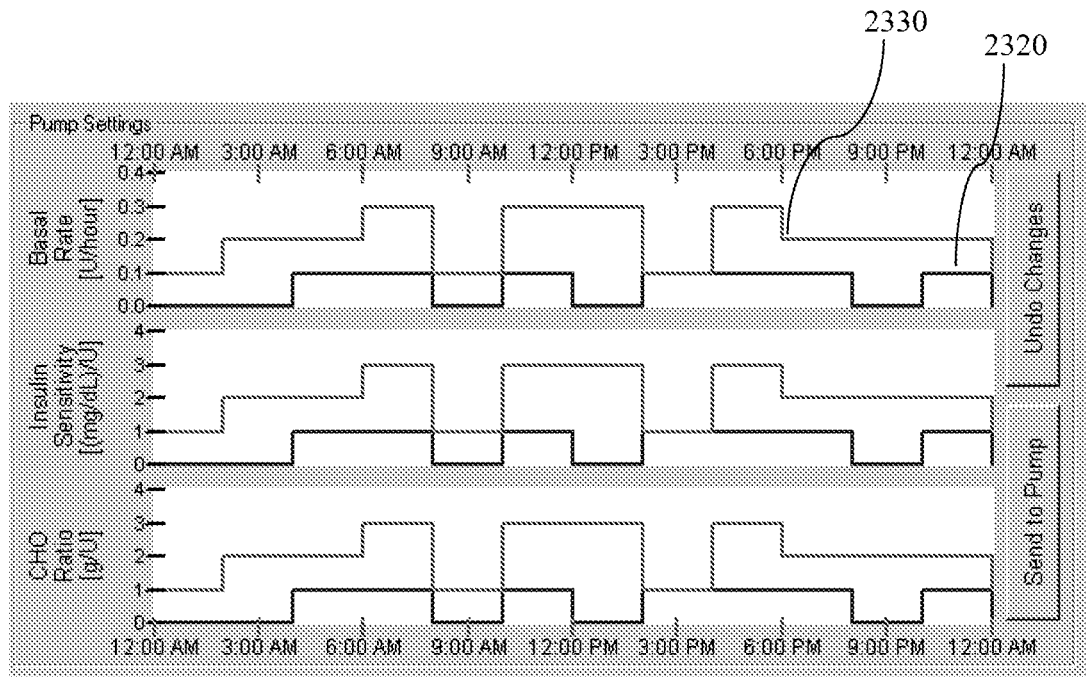
FIG. 22 is an exemplary screen display of a medication delivery profile.
Figure 23:
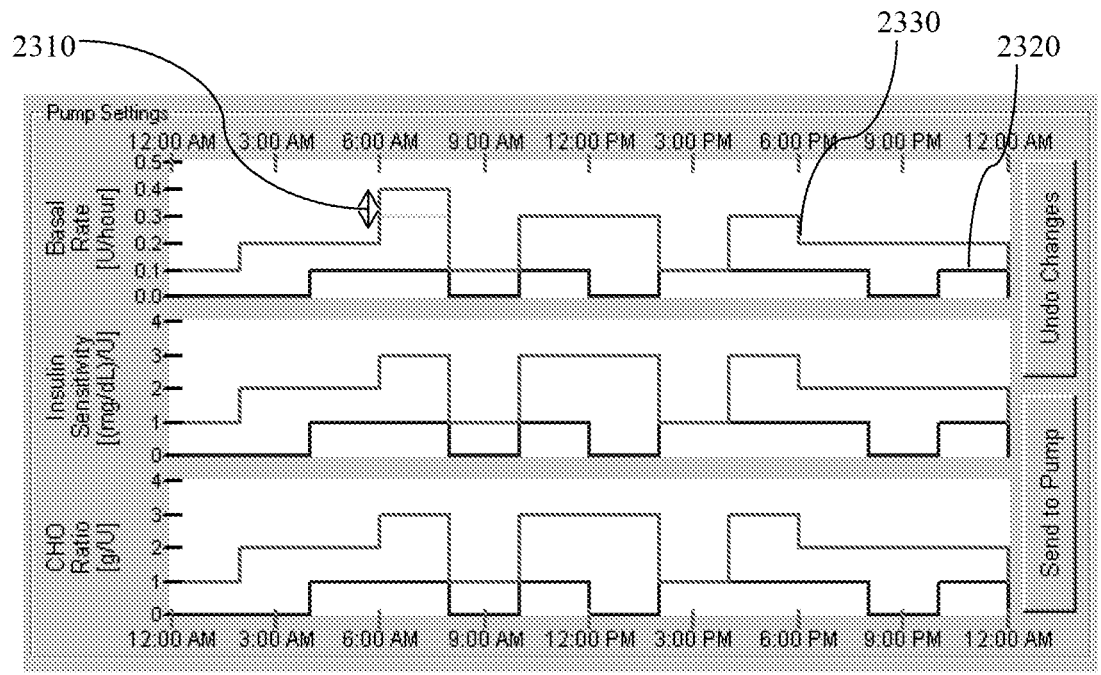
FIG. 23 is an exemplary screen display illustrating vertical modification of the medication delivery profile.
Figure 24:
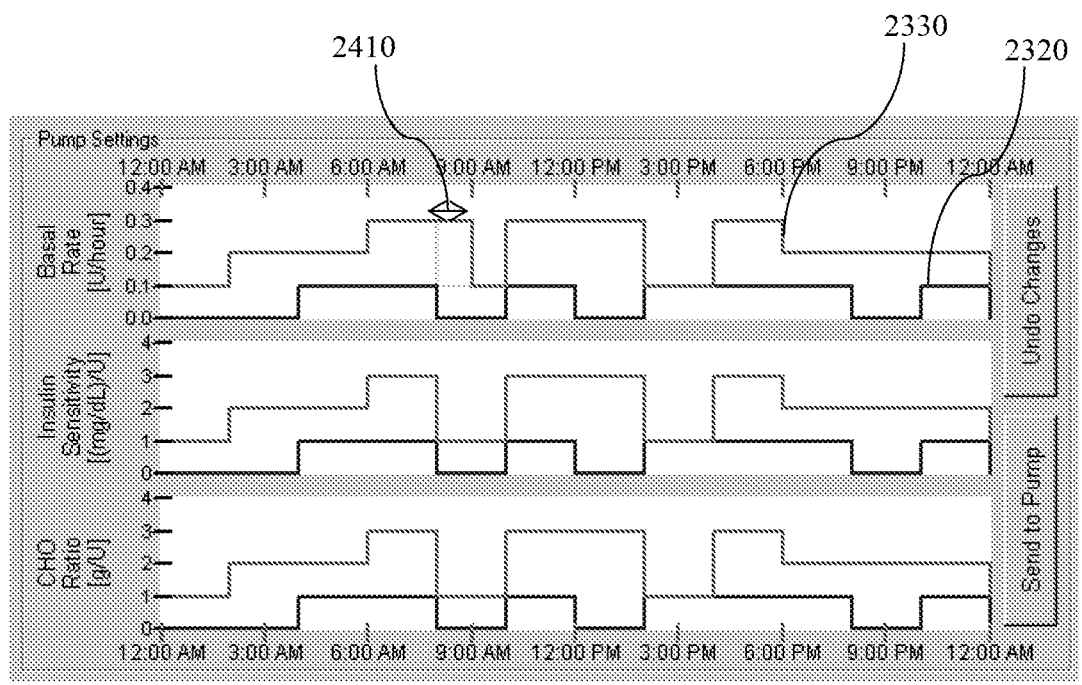
FIG. 24 is an exemplary screen display illustrating horizontal modification of the medication delivery profile.
Figure 25:
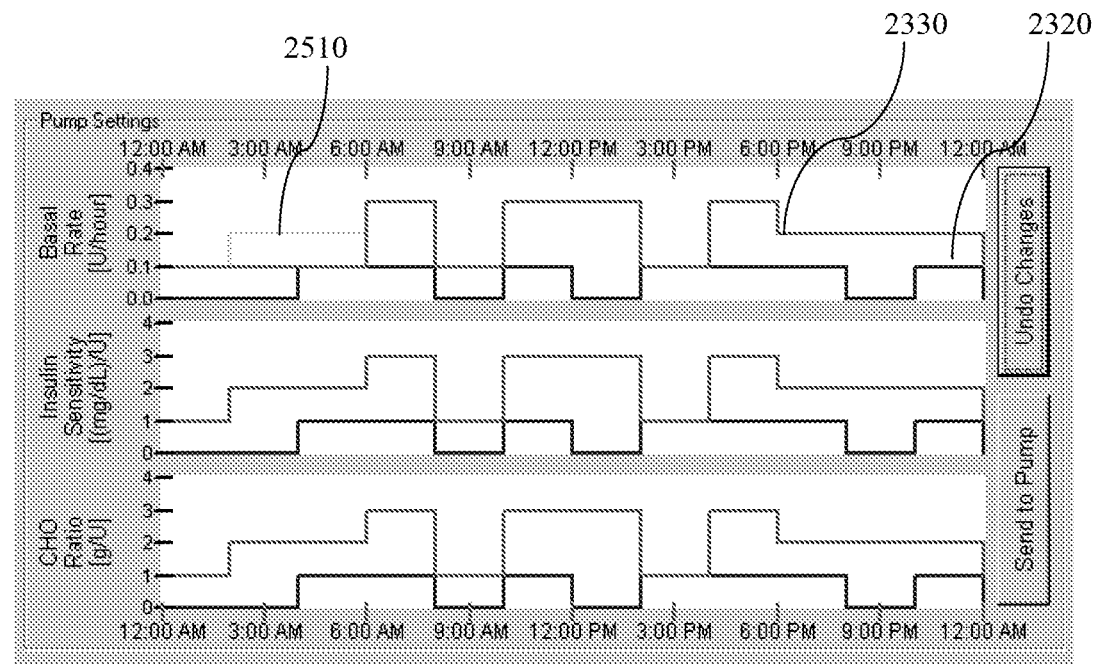
FIG. 25 is an exemplary screen display illustrating addition of a transition in the medication delivery profile.
Figure 26:
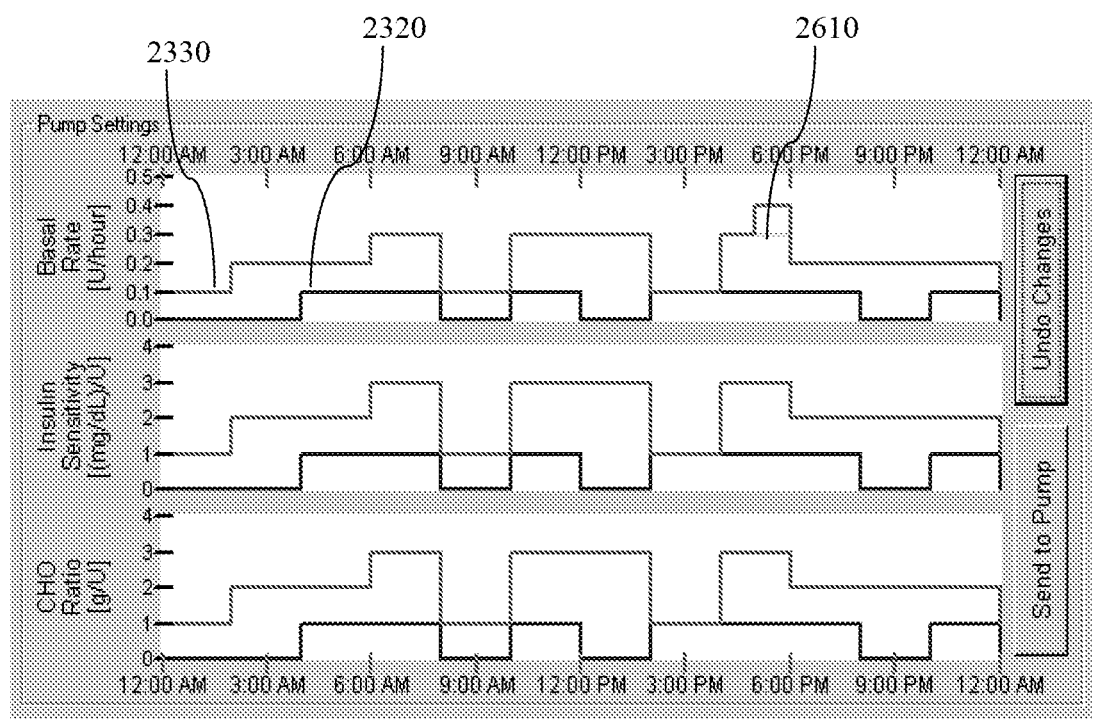
FIG. 26 is an exemplary screen display illustrating deletion of a transition in the medication delivery profile.

FIG. 22 is an exemplary screen display of a medication delivery profile. As can be seen, in one aspect, the basal rate, insulin sensitivity and the insulin to carbohydrate ratio (CHO) are shown on the Y-axis, while the X-axis represents the corresponding time of day. For each of these therapy parameters, the existing profile is shown 2320 and the optimal profile proposed by the therapy calculator is shown 2330. FIG. 23 is an exemplary screen display illustrating vertical modification of the proposed medication delivery profile as shown by the directional arrow 2310, while FIG. 24 illustrates an exemplary screen display with horizontal modification of the proposed medication delivery profile shown by the directional arrow 2410. Referring still to the Figures, FIG. 25 illustrates addition of a transition 2510 in the medication delivery profile, while FIG. 26 illustrates deletion 2610 of a transition in the medication delivery profile.

In this manner, in one aspect, the visual modeling and dynamic feedback in therapy management provides immediate feedback on the anticipated results or effect of a proposed modification to the therapy profile such as increase or decrease of insulin administration to the patient. Accordingly, the patient, the physician or the healthcare provider may be provided with a graphical treatment tool to assist in the treatment of the patient's condition.

In another aspect, the visual modeling and dynamic feedback in the therapy management includes illustration of a current physiological profile such as the glucose level and one or more time corresponding parameter values associated with the current physiological profile such that, when the user, patient or healthcare provider modifies the displayed one or more parameter values (such as, but not limited to, the corresponding medication level including basal profile, insulin sensitivity, and/or insulin to carbohydrate ratio), the corresponding current physiological profile is responsively modified and displayed in real time, while leaving a trace (referred to herein as a phantom plot) of the current physiological profile and the time corresponding one or more parameter values associated with the current physiological profile.

That is, by manipulating the display of the therapy related parameter value to a modified level (for example, using a conventional click and drag operation of an input device such as a computer mouse), the displayed current physiological profile is modified on the screen accordingly, while maintaining the display of the current physiological profile as well as the initial or current therapy related parameter value. In other words, in one aspect, the display or screen is configured to represent both the initial profile and the modified profile so that the user, patient or healthcare provider can readily see the change to the plotted physiological profile in response to the modification to the one or more parameter values, for example, the initial profile or plot shown as a lighter trace (phantom plot) or of a different color or representation, while maintaining a darker color or thickness of the plot for the modified profile/plot.

For example, with a plot of a glucose level information and a corresponding basal profile on the screen, when the user, patient or the healthcare provider selects the basal profile and moves or modifies one or more sections of the basal profile, the initial position of the glucose level remains displayed as a trace (phantom plot), while displaying the new or modified glucose level. In addition, both the initial and the modified basal profile of the time corresponding basal profile are displayed on the same chart or plot. In this manner, in one aspect, the display of the remote terminal 140 (FIG. 1) and/or the display of the analyte monitoring system 110 or the display of the fluid delivery device 120 may be manipulated using, for example, user interface capabilities such as an input device (computer mouse for use with the remote terminal 140), input/select buttons on the analyte monitoring system 110 or the fluid delivery device 120 to provide visual indications of the extent of adjustment to one or more parameters from the initial or recommended settings or profiles and the corresponding modification to the associated physiological or other monitored profile such as glucose levels in addition to the initial displayed profile.

Figure 27:
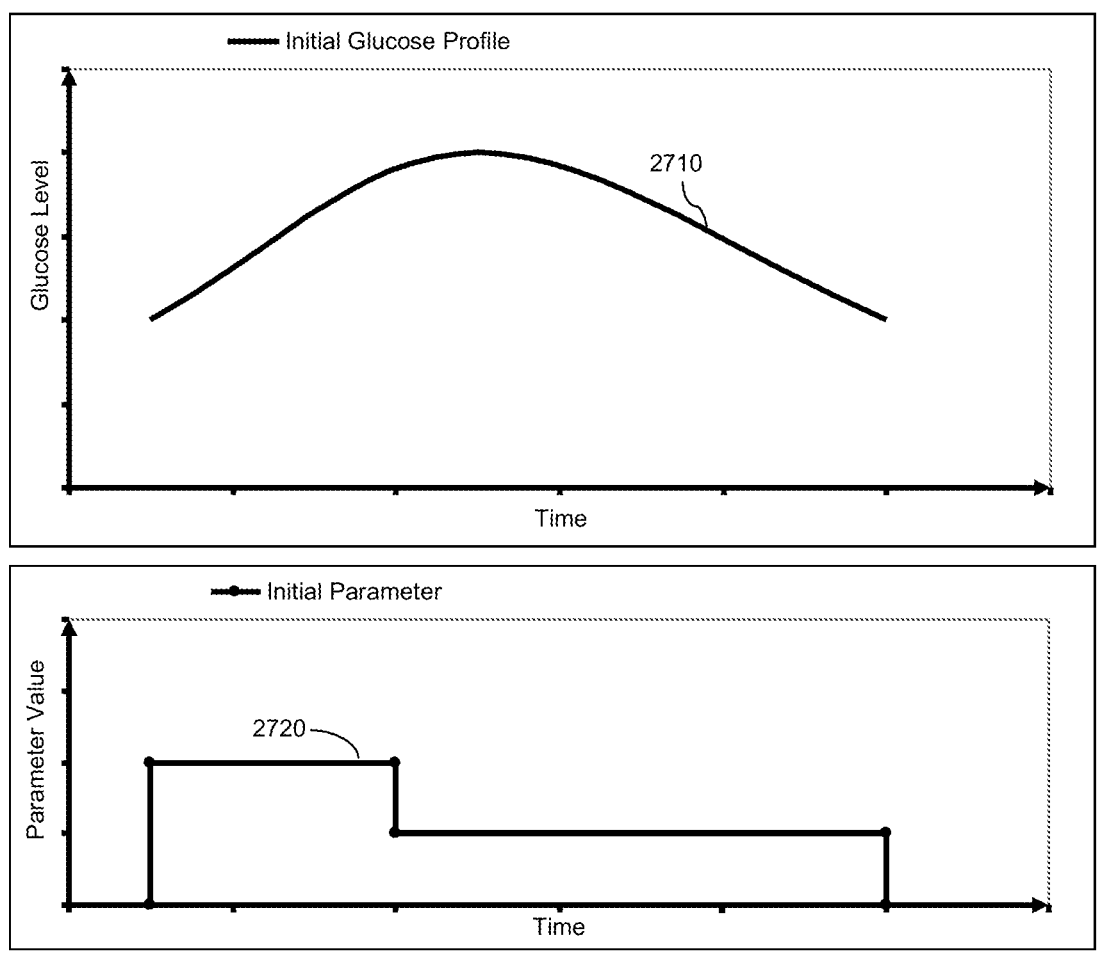
FIG. 27 is an exemplary display illustrating an initial glucose level and a corresponding parameter value as a function of time in one embodiment.
Figure 28:
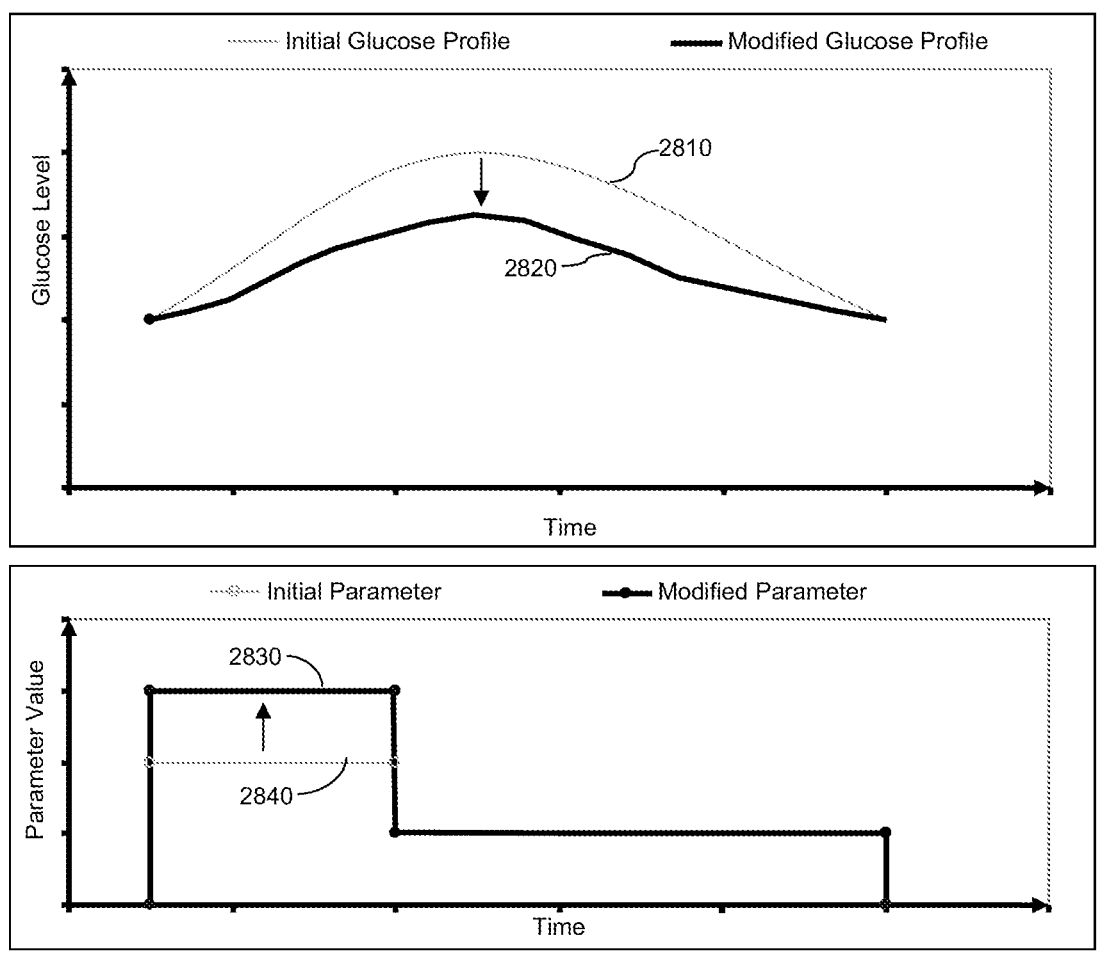
FIG. 28 is an exemplary display illustrating response to the manipulation of the initial parameter value of FIG. 27 and corresponding modification to the displayed glucose profile as a function of time in one embodiment.
Figure 29:
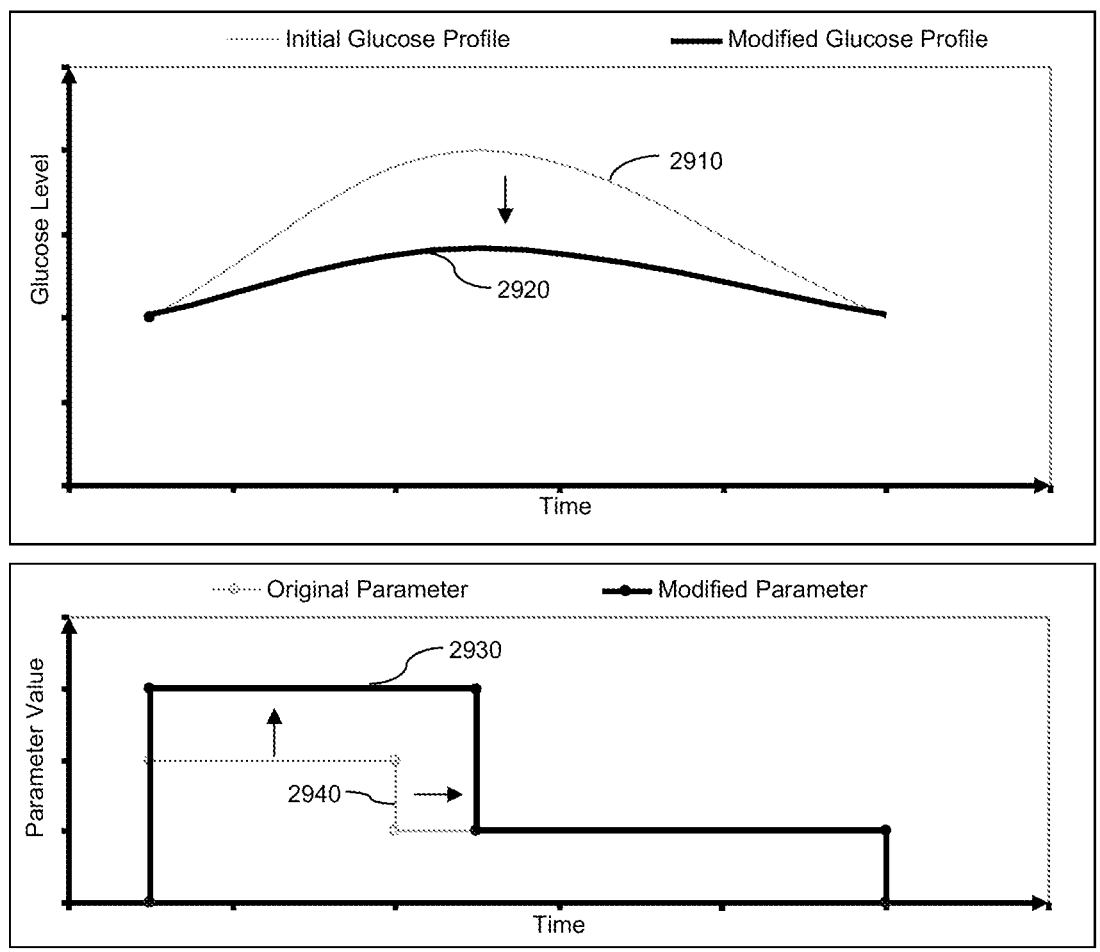
FIG. 29 is an exemplary display illustrating response to the manipulation of the initial parameter value of FIG. 27 and corresponding modification to the displayed glucose profile as a function of time in another embodiment.

FIG. 27 is an exemplary display illustrating an initial glucose level and a corresponding parameter value, and FIGS. 28-29 are exemplary displays illustrating response to the manipulation of the parameter plot or value segment of FIG. 27 and corresponding modification to the displayed glucose profile as a function of time in one embodiment. Referring to FIGS. 27-29, an initial display of one parameter value 2720 (FIG. 27) is plotted along with a time corresponding plot of the glucose level 2710 (FIG. 27). In one aspect, the user, patient or the healthcare provider may move the computer mouse to position the cursor over and select a segment of the plotted parameter value 2720 (for example, between two displayed dots at each transition point in the displayed plot). With the selected segment of the plotted parameter, the user, patient or the healthcare provider may move the selected segment in a vertical direction as shown in FIG. 28, in a horizontal direction, or in both a horizontal and vertical direction as shown in FIG. 29.

Referring back to FIG. 28, when the selected segment of the displayed parameter 2840 is moved in an upward vertical direction to a new position 2830 as shown, the corresponding initial glucose profile 2810 is updated to the modified glucose profile 2820. As shown in FIG. 28, it can be seen that both the initial position and the modified position of the parameter plot and those of the glucose levels are shown. In particular, in one embodiment, when a modification to the parameter value is effected, the segment of the initial position or plot of the parameter value (and the corresponding initial display of the glucose level) is displayed as a lighter trace or of a different color (for example, the initial parameter segment 2840 and the initial glucose profile 2810) to be distinguishable with the modified parameter segment 2830 and the corresponding modified glucose profile 2820. In one aspect, the particular type of display modes (different color, thickness, legend indicating the initial and modified chart or profile segment) may be user definable or configurable.

Referring to FIG. 29, when a segment 2940 of the parameter displayed is modified in both the vertical and the horizontal direction to the modified position 2930 as shown, the corresponding displayed initial glucose level display 2910 is updated to a modified profile 2920 in the direction shown by the arrow illustrating a movement from the initial display 2910 to the modified display 2920 in addition to the display of the initial glucose profile 2910 and the initial parameter value 2940.

In this manner, in one aspect, proposed or recommended modification to therapy profiles such as basal profiles may be displayed including the initial and modified profiles, and the corresponding initial and modified physiological profiles recalculated or determined in response to the proposed or recommended modification to the therapy profiles may be visually output to the user, patient or the healthcare provider to enhance visual representation of the proposed or recommended modification to the therapy profiles in the course of the treatment and therapy of physiological conditions such as diabetes. In this manner, the user, patient or the healthcare provider may easily and visually understand the degree of parameter change and effect of the change on the output values such as insulin delivery and glucose level.

While a single parameter plot is shown in conjunction with the discussion above and FIGS. 27-29, in accordance with the embodiments of the present disclosure, multiple parameter values or profiles may be displayed and modified by the user, patient, or the healthcare provider. In such cases, for each parameter displayed, when a modification to the parameter is performed, both the initial and the modified profile or plot may be displayed. Moreover, while glucose level is discussed above in the physiological profile displayed, embodiments of the present disclosure may be used to display other physiological profiles and associated parameters that affect the physiological profile, such as blood pressure level or other physiological conditions.

In accordance with the embodiments of the present disclosure, other variations of the embodiments discussed above are contemplated. For example, the phantom plots may be associated with the plots that are adjusted rather than the plots that stay in the same position. Also, as discussed above, the phantom plots may be represented other than as a thinner line (compared to the non-phantom or the modified profile), including, such as, for example, with different colors, line types, icon indication, legends, labels and the like. In addition, the modification to the initial profile or parameter may be represented in tabular form with numeric value entries, with some table elements associated with the original or initial values and other table elements representing the adjusted/modified values.

In a further embodiment, for multiple adjustments or modifications, the phantom (original) plot may be updated or modified after each adjustment, relative to the immediately prior modification position. In this case, optionally, multiple phantom plots may be displayed (using different indications such as gradually increasing thickness of the plotted line, or different color or legend, for example) such that the modifications may be visually represented in a graphically sweeping manner, illustrating each modification to the parameter(s) and the corresponding modification to the physiological profile in, for example, a single chart or display.

Moreover, other mechanisms may be contemplated to allow the user, patient or the healthcare provider to make the adjustments to the parameters. For example, a table may be provided and displayed with numeric values associated with parameter segments, and the user, patient or the healthcare provider may edit the numeric values in the table. After the adjustment or modification to the numeric value in the table, the corresponding plots may be modified as described above, in a similar manner as when the graphical segment is modified using, for example, the computer mouse by click and drag operation.

In addition, adjustment or modification to the parameters may be performed in other manner. For example, segments of the parameter plots may be predefined, for instance, at a segment of 15 minutes or other time periods. Alternatively, the segments may be defined by changes in time for the original parameter value. Additionally, new segments may be defined by the user using for example, the computer mouse by clicking the mouse button with a cursor near a point on the parameter plot, where the selected or clicked point representing the end of a segment with the beginning of a segment already defined on the plot (as indicated by a dot on the plot). Also, a segment may be defined by the user with a mouse click once near one point on a plot and again near a second point, where the points define a segment. In this aspect, the segment may be visually highlighted (for example, made thicker) to indicate to the user that it can be dragged or otherwise adjusted or modified. Furthermore, these defined segments may be limited to a predefined time resolution as defined by the insulin delivery device, for example. That is, fluid delivery device 120 (FIG. 1) may be limited to a 15 minute resolution of parameter changes, in which case, the plotting routine may locate the 15 minute point on the plot closest to where the user selected with the mouse.

In another aspect, the display discussed above may include one or more error indication. For example, the glucose display may show, along with the median glucose profile, the upper and lower glucose quartiles. This information may be useful to the user when making corresponding adjustments to the therapy profile. For example, if the user, patient or the healthcare provider desires to make parameter adjustments in order to lower the median glucose profile, they may understand from the lower quartile plot that there is a high degree of glucose variation and that it may not be safe or desirable to lower the median profile as much as they intended or desired. In one aspect, the phantom plots discussed above may be associated with these types of displayed error indications.

As described above, the profile modification and the corresponding displays may be based on data organized around time-of-day information. In another aspect, the modifications or determinations and the corresponding display plots may be based on meal markers or meal bolus events recorded in time. These events may be entered into the system manually (for instance a meal event may be entered into the system by the user) or automatically (the system may record a meal bolus when it is delivered, using, for example, the fluid delivery device 120). The parameter, insulin delivery and glucose data may be organized in data sets, with time relative to the meal bolus event. A resulting data set for each may be generated using a median calculation or average calculation, or other appropriate calculation, to generate a profile in time relative to the meal bolus event. For example, each data set may be defined one hour prior to and 5 hours after when meals bolus event occurs. Adjustments, as described above for plots over time-of-day, may be made similarly for plots over time-relative-to-meal-events. Also, determination and display of parameters, insulin delivery and glucose profiles may be made for data sets generated relative to correction bolus events.

In one aspect, the user may select from a list of possible parameters to adjust or modify based on one or more indications presenting the parameters available for modification. For example, if the basal parameter adjustment is selected, then the determination or modification and display may be associated with time-of-day. In this case, when the user adjusts the glucose values, the basal profile parameter may be adjusted to correlate with glucose level adjustments. As a further example, if the carbohydrate ratio parameter is selected, the modification and display may be associated with time relative to meal bolus or meal events. As yet a further example, when the insulin sensitivity parameter adjustment is selected, the modification and display may be associated with time relative to a correction bolus.

Additionally, when modifications and displays are associated with time relative to an event, they may be restricted to time of day periods. For example, the profile modification determination may be restricted to one or more meal bolus that occurs in a morning period, for instance, between 6 am and 11 am. This restriction may be used to associate a single carbohydrate ratio parameter for this time period. Also, the resulting modified parameters may be constrained by resolution restrictions imposed by the insulin delivery device 120 discussed above.

In an alternative embodiment, the parameter and/or physiological profile display may include both actual and recommended glucose traces, insulin traces and therapy parameter traces, in addition to the modified traces, and further, may be user definable or configurable.

Within the scope of the present disclosure, data mining techniques may be used to generate and/or modify the physiological profile models based on the patient's data as well as data from other patient's that have similar physiological characteristics. Such data mining techniques may be used to filter and extract physiological profile models that meet a predetermined number of criteria and ranked in a hierarchy of relevance or applicability to the particular patient's physiological condition. The simulation module may be implemented by computer software with algorithm that defines the parameters associated with the patient's physiological conditions, and may be configured to model the various different conditions of the patient's physiology.

Within the scope of the present disclosure, the therapy analysis system described above may be implemented in a database management system and used for treatment of diabetic patients by a general practitioner. Additionally, the therapy analysis system may be implemented based on multiple daily doses of insulin (using, for example, syringe type insulin injector, or inhalable insulin dispenser) rather than based on an insulin pump, where the insulin related information may be recorded by the patient and uploaded or transferred to the data management system (for example, the remote terminal 140 (FIG. 1)). Also, some or all of the data analysis and display described above may be performed by the analyte monitoring system 110 (FIG. 1) or the fluid delivery device 120, or by a separate controller configured for communication with the therapy management system 100.

In one embodiment, a method may comprise displaying a first representation of a medication treatment parameter profile, displaying a first representation of a physiological profile associated with the medication treatment parameter profile, detecting a modification to a segment of the medication treatment parameter profile, displaying a modified representation of the medication treatment parameter profile and the physiological profile based on the detected modification to the segment of the medication treatment parameter profile, modifying an attribute of the first representation of the medication treatment parameter profile, and modifying an attribute of the first representation of the physiological profile.

In one aspect modifying the attribute of the first representation of the medication treatment parameter profile may include modifying a visual attribute without modifying the underlying value associated with the profile.

Moreover, the visual attribute may include one or more of a color representation, a line representation, visual contrast representation.

In another aspect, the modified representation and the first representation of the medication treatment parameter profile may include at least an overlapping displayed segment.

In yet another aspect the modified representation and the first representation of the physiological profile may be substantially non-overlapping.

In one aspect, the medication treatment parameter profile may include one or more of a basal rate profile, an insulin sensitivity profile, an insulin to carbohydrate ratio, a meal event, a bolus event, or an insulin type profile.

In another aspect, the physiological profile may include a glucose level profile, an oxygen level profile, or a blood pressure level profile.

In yet another aspect, modifying the attribute of the first representation of the physiological profile may include modifying a visual attribute without modifying the underlying value associated with the profile.

Moreover, when the attribute of the first representation of the medication treatment parameter profile is modified, the displayed position of the first representation of the medication treatment parameter profile is not changed.

Moreover, when the attribute of the first representation of the physiological profile is modified, the displayed position of the first representation of the physiological profile is not changed.

Furthermore, the displayed first representation of the medication treatment parameter profile and the physiological profile respectively may include one or more of a line graph, a bar graph, a 2-dimensional graph, or a 3-dimensional graph.

In another embodiment, an apparatus may comprise, a display unit, one or more processing units coupled to the display unit, and a memory for storing instructions which, when executed by the one or more processing units, may cause the one or more processing units to display a first representation of a medication treatment parameter profile, display a first representation of a physiological profile associated with the medication treatment parameter profile, detect a modification to a segment of the medication treatment parameter profile, display a modified representation of the medication treatment parameter profile and the physiological profile based on the detected modification to the segment of the medication treatment parameter profile, modify an attribute of the first representation of the medication treatment parameter profile, and modify an attribute of the first representation of the physiological profile.

In one aspect, the memory for storing instructions which, when executed by the one or more processing units, may cause the one or more processing units to modify a visual attribute associated with the physiological profile without modifying the underlying value associated with the first representation of the physiological profile, and to modify a visual attribute associated with the first representation of the medication treatment parameter profile without modifying the underlying value associated with the medication treatment parameter profile.

Moreover, the visual attribute may include one or more of a color representation, a line representation, visual contrast representation.

In another aspect, the modified representation and the first representation of the medication treatment parameter profile may include at least an overlapping displayed segment.

Furthermore, the modified representation and the first representation of the physiological profile may be substantially non-overlapping.

In yet another aspect, the medication treatment parameter profile may include one or more of a basal rate profile, an insulin sensitivity profile, an insulin to carbohydrate ratio, a meal event, a bolus event, or an insulin type profile.

Moreover, the physiological profile may include a glucose level profile, an oxygen level profile, or a blood pressure level profile.

In yet another aspect, when the attribute of the first representation of the medication treatment parameter profile is modified, the displayed position of the first representation of the medication treatment parameter profile may not be changed, and further, when the attribute of the first representation of the physiological profile is modified, the displayed position of the first representation of the physiological profile may not be changed.

The various processes described above including the processes performed by the processor 210 (FIG. 2) in the software application execution environment in the fluid delivery device 120 (FIG. 1) as well as any other suitable or similar processing units embodied in the analyte monitoring system 110, the fluid delivery device 120, and/or the remote terminal 140, including the processes and routines described in conjunction with FIGS. 3-16, may be embodied as computer programs developed using an object oriented language that allows the modeling of complex systems with modular objects to create abstractions that are representative of real world, physical objects and their interrelationships. The software required to carry out the inventive process, which may be stored in the memory unit 240 (or similar storage devices in the analyte monitoring system 110 and the remote terminal 140) and executed by the processor 210, may be developed by a person of ordinary skill in the art and may include one or more computer program products.

Various other modifications and alterations in the structure and method of operation of this disclosure will be apparent to those skilled in the art without departing from the scope and spirit of the disclosure. Although the present disclosure has been described in connection with specific preferred embodiments, it should be understood that the present disclosure as claimed should not be unduly limited to such specific embodiments. It is intended that the following claims define the scope of the present disclosure and that structures and methods within the scope of these claims and their equivalents be covered thereby.

What is claimed is:

1. A non-transitory computer readable medium, containing instructions for causing a processor to perform a method of determining a customized estimated insulin bolus amount for a user, the method comprising:
receiving current user meal data about a meal consumed during a meal time period;
receiving current user insulin data about insulin provided to the user during the meal time period;
receiving current user glucose concentration data from a continuous glucose monitoring system;
querying at least stored past user meal data during a past meal time period, wherein the current user meal data and the stored past user meal data are comparable in at least one of a meal type or a meal size;
customizing an estimated insulin bolus amount based on at least the current user meal data, the current user insulin data, and the current user glucose concentration data compared to at least the stored past user meal data; and
transmitting a command to administer the customized estimated insulin bolus amount to an insulin delivery device.

2. The medium of claim 1, wherein the current user meal data and the stored past user meal data comprises the meal size.

3. The medium of claim 1, wherein the current user meal data and the stored past user meal data comprises the meal type.

4. The medium of claim 3, wherein the meal type comprises data including one or more of fat content, carbohydrate content, or protein content.

5. The medium of claim 1, wherein the customizing further comprises customizing a time for bolus delivery.

6. The medium of claim 1, further comprising:
receiving exercise data for determining whether the user has exercised; and
querying at least stored past exercise data, wherein customizing an estimated insulin bolus amount is further based on the exercise data.

7. The medium of claim 1, further comprising displaying a graphic of at least the customized estimated insulin bolus amount.

8. The medium of claim 7, wherein the graphic comprises a prompt for the user to perform an action.

9. The medium of claim 1, wherein the receiving current user insulin data includes receiving data from the insulin delivery device.

10. An insulin delivery device programmed to provide a customized estimated insulin bolus amount, the customized estimated insulin bolus amount incorporating learned user data, the programming performing a method comprising:
receiving current user meal data about a meal consumed during a meal time period;
receiving current user insulin data about insulin provided to the user during the meal time period;
receiving current user glucose concentration data from a continuous glucose monitoring system;
querying at least stored past user meal data during a past meal time period, wherein the current user meal data and the stored past user meal data are comparable in at least one of a meal type or a meal size;
customizing an estimated insulin bolus amount based on at least the current user meal data, the current user insulin data, and the current user glucose concentration data compared to at least the stored past user meal data;
displaying the customized estimated insulin bolus amount on a display of the insulin delivery device for user confirmation; and
delivering the customized estimated insulin bolus amount upon user confirmation.

11. A continuous glucose monitoring system programmed to provide a customized estimated insulin bolus amount, the customized estimated insulin bolus amount incorporating learned user data, the programming performing a method comprising:
receiving current user meal data about a meal consumed during a meal time period;
receiving current user insulin data about insulin provided to the user during the meal time period;
receiving current user glucose concentration data from the continuous glucose monitoring system;
querying at least stored past user meal data during a past meal time period, wherein the current user meal data and the stored past user meal data are comparable in at least one of a meal type or a meal size;
customizing an estimated insulin bolus amount based on at least the current user meal data, the current user insulin data, and the current user glucose concentration data compared to at least the stored past user meal data;
displaying the customized estimated insulin bolus amount on a display of the glucose monitoring system for user confirmation; and
transmitting the customized estimated insulin bolus amount upon user confirmation to an insulin delivery device for insulin delivery to the user.

* * * * *